（12） United States Patent
Sloan et al.

(10) Patent No.: US 11,633,127 B2
(45) Date of Patent: *Apr. 25, 2023

(54) METHODS, DEVICES, AND SYSTEMS RELATED TO ANALYTE MONITORING

(71) Applicant: ABBOTT DIABETES CARE INC., Alameda, CA (US)

(72) Inventors: Mark K. Sloan, Redwood City, CA (US); Royce Cheng, San Francisco, CA (US); Gary A. Hayter, Oakland, CA (US); Marc B. Taub, Mountain View, CA (US); Mani Gopal, Hillsborough, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/950,595

(22) Filed: Nov. 17, 2020

(65) Prior Publication Data

US 2021/0068716 A1      Mar. 11, 2021

Related U.S. Application Data

(63) Continuation of application No. 17/073,589, filed on Oct. 19, 2020, which is a continuation of application
(Continued)

(51) Int. Cl.
*A61B 5/145* (2006.01)
*G16H 40/63* (2018.01)
(Continued)

(52) U.S. Cl.
CPC .......... *A61B 5/145* (2013.01); *A61B 5/14532* (2013.01); *A61B 5/7221* (2013.01);
(Continued)

(58) Field of Classification Search
CPC . A61B 5/14503; A61B 2562/08; A61B 5/145; A61B 5/14507; A61B 5/14532;
(Continued)

(56) References Cited

U.S. PATENT DOCUMENTS 4,942,877 A   7/1990   Sakai et al.
5,262,035 A   11/1993  Gregg et al.
(Continued)

FOREIGN PATENT DOCUMENTS

WO    WO 2009/146445 A1   12/2009
WO    WO 2015/153482 A1   10/2015
WO    WO 2016/179559 A2   11/2016

OTHER PUBLICATIONS

EP, 13859365.2 Extended European Search Report, dated Jul. 5, 2016.
(Continued)

*Primary Examiner* — Puya Agahi
(74) *Attorney, Agent, or Firm* — Sterne, Kessler, Goldstein & Fox P.L.L.C.

(57) ABSTRACT

Generally, methods, devices, and systems related to analyte monitoring and data logging are provided—e.g., as related to in vivo analyte monitoring devices and systems. In some aspects, methods, devices, and systems are provided that relate to enable related settings based on an expected use of an in vivo positioned sensor; logging or otherwise recording analyte levels acquired or derived—e.g., sample analyte levels more frequently than they are logged or otherwise recorded in memory; dynamically adjust the data logging frequency; randomly determine times of acquiring or storing analyte levels from the in-vivo positioned analyte sensors; and enable recording related settings when the system is operable.

20 Claims, 11 Drawing Sheets

Related U.S. Application Data

No. 15/868,890, filed on Jan. 11, 2018, now Pat. No. 10,806,382, which is a continuation of application No. 14/092,035, filed on Nov. 27, 2013, now Pat. No. 9,872,641.

(60) Provisional application No. 61/731,316, filed on Nov. 29, 2012.

(51) Int. Cl.
*G16H 10/40* (2018.01)
*A61B 5/00* (2006.01)
*A61B 5/1495* (2006.01)

(52) U.S. Cl.
CPC .............. *G16H 10/40* (2018.01); *G16H 40/63* (2018.01); *A61B 5/1495* (2013.01); *A61B 5/14503* (2013.01); *A61B 2560/029* (2013.01); *A61B 2562/08* (2013.01)

(58) Field of Classification Search
CPC .. A61B 5/14546; A61B 5/1495; G16H 10/40; G16H 40/63
See application file for complete search history.

(56) References Cited

U.S. PATENT DOCUMENTS

| | | | |
|---|---|---|---|
| 5,262,305 A | 11/1993 | Heller et al. | |
| 5,264,104 A | 11/1993 | Gregg et al. | |
| 5,320,725 A | 6/1994 | Gregg et al. | |
| 5,593,852 A | 1/1997 | Heller et al. | |
| 5,720,293 A | 2/1998 | Quinn et al. | |
| 5,987,343 A | 11/1999 | Kinast | |
| 6,175,752 B1 | 1/2001 | Say et al. | |
| 6,308,089 B1 | 10/2001 | von der Ruhr et al. | |
| 6,515,273 B2 | 2/2003 | Al-Ali | |
| 6,650,471 B2 | 11/2003 | Doi | |
| 6,746,582 B2 | 6/2004 | Heller et al. | |
| 7,399,277 B2 | 7/2008 | Saidara et al. | |
| 7,670,263 B2 | 3/2010 | Ellis et al. | |
| 7,684,872 B2 | 3/2010 | Carney et al. | |
| 7,811,231 B2 | 10/2010 | Jin et al. | |
| 7,894,869 B2 | 2/2011 | Hoarau | |
| 8,478,406 B2 | 7/2013 | Burnes et al. | |
| 8,567,393 B2 | 10/2013 | Hickle et al. | |
| 8,821,792 B2 | 9/2014 | Drucker et al. | |
| 9,143,569 B2 | 9/2015 | Mensinger et al. | |
| 9,215,980 B2 | 12/2015 | Tran et al. | |
| 9,339,197 B2 | 5/2016 | Griswold et al. | |
| 9,414,775 B2 | 8/2016 | Colvin, Jr. et al. | |
| 9,446,194 B2 | 9/2016 | Kamath et al. | |
| 9,452,258 B2 | 9/2016 | Dobbles et al. | |
| 9,717,421 B2 | 8/2017 | Griswold et al. | |
| 9,814,400 B1 | 11/2017 | Cendrillon et al. | |
| 10,159,432 B1 | 12/2018 | Pathak et al. | |
| 10,209,817 B1 | 2/2019 | Cazzoli et al. | |
| 10,264,971 B1 | 4/2019 | Kennedy et al. | |
| 2003/0208113 A1 | 11/2003 | Mault et al. | |
| 2004/0078219 A1 | 4/2004 | Kaylor et al. | |
| 2004/0158294 A1 | 8/2004 | Thompson | |
| 2005/0038680 A1 | 2/2005 | McMahon | |
| 2005/0075675 A1 | 4/2005 | Mulligan et al. | |
| 2005/0171410 A1* | 8/2005 | Hjelt ................. | A61B 5/00 128/920 |
| 2006/0016700 A1 | 1/2006 | Brister et al. | |
| 2006/0019397 A1 | 1/2006 | Soykan | |
| 2006/0173260 A1 | 8/2006 | Gaoni et al. | |
| 2006/0229511 A1 | 10/2006 | Fein et al. | |
| 2006/0270421 A1 | 11/2006 | Phillips et al. | |
| 2007/0015976 A1 | 1/2007 | Miesel et al. | |
| 2007/0150024 A1* | 6/2007 | Leyde ................... | G16H 20/30 607/45 |
| 2007/0255166 A1 | 11/2007 | Carney et al. | |
| 2007/0255352 A1 | 11/2007 | Roline et al. | |
| 2007/0255353 A1 | 11/2007 | Reinke et al. | |
| 2007/0265666 A1 | 11/2007 | Roberts et al. | |
| 2007/0265668 A1 | 11/2007 | Reinke et al. | |
| 2007/0265671 A1 | 11/2007 | Roberts et al. | |
| 2007/0265674 A1 | 11/2007 | Olson et al. | |
| 2008/0125701 A1 | 5/2008 | Moberg et al. | |
| 2008/0161664 A1 | 7/2008 | Mastrototaro et al. | |
| 2008/0221930 A1 | 9/2008 | Wekell et al. | |
| 2008/0234562 A1 | 9/2008 | Jina | |
| 2008/0255635 A1 | 10/2008 | Bettesh et al. | |
| 2008/0278331 A1* | 11/2008 | Hayter ................. | A61B 5/0015 340/573.1 |
| 2008/0288180 A1* | 11/2008 | Hayter ................. | A61B 5/7275 702/23 |
| 2008/0319295 A1 | 12/2008 | Bernstein et al. | |
| 2009/0069642 A1* | 3/2009 | Gao ....................... | H04L 67/12 600/300 |
| 2009/0093687 A1 | 4/2009 | Telfort et al. | |
| 2009/0160642 A1* | 6/2009 | Kim ..................... | A61B 5/0002 340/539.22 |
| 2009/0192366 A1 | 7/2009 | Mensinger et al. | |
| 2009/0192745 A1 | 7/2009 | Kamath et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0247849 A1 | 10/2009 | McCutcheon et al. | |
| 2009/0312615 A1* | 12/2009 | Caduff ............... | A61B 5/14532 600/316 |
| 2009/0318792 A1 | 12/2009 | Fennell et al. | |
| 2010/0023081 A1 | 1/2010 | Audet et al. | |
| 2010/0033303 A1 | 2/2010 | Dugan et al. | |
| 2010/0094111 A1 | 4/2010 | Heller et al. | |
| 2010/0191153 A1* | 7/2010 | Sanders ................ | A61B 5/4585 600/587 |
| 2010/0213057 A1 | 8/2010 | Feldman et al. | |
| 2010/0274515 A1 | 10/2010 | Hoss et al. | |
| 2010/0327057 A1 | 12/2010 | Medina et al. | |
| 2011/0054282 A1* | 3/2011 | Nekoomaram .......... | G01K 1/02 600/347 |
| 2011/0124996 A1 | 5/2011 | Reinke et al. | |
| 2011/0184265 A1 | 7/2011 | Hayter | |
| 2011/0193704 A1 | 8/2011 | Harper et al. | |
| 2011/0237960 A1 | 9/2011 | Rantala | |
| 2011/0257495 A1 | 10/2011 | Hoss et al. | |
| 2011/0287528 A1* | 11/2011 | Fern ....................... | G16H 40/67 435/287.1 |
| 2012/0088995 A1 | 4/2012 | Fennell et al. | |
| 2012/0108934 A1 | 5/2012 | Valdes et al. | |
| 2012/0157801 A1 | 6/2012 | Hoss et al. | |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2012/0262298 A1 | 10/2012 | Bohm et al. | |
| 2012/0323099 A1 | 12/2012 | Mothilal et al. | |
| 2013/0043974 A1 | 2/2013 | Hyde et al. | |
| 2013/0085358 A1 | 4/2013 | Crouther et al. | |
| 2013/0132330 A1 | 5/2013 | Hurwitz et al. | |
| 2013/0179110 A1* | 7/2013 | Lee ....................... | A61B 5/1118 702/130 |
| 2013/0198685 A1 | 8/2013 | Bernini et al. | |
| 2013/0217979 A1* | 8/2013 | Blackadar ........... | A61B 5/14532 600/301 |
| 2013/0253309 A1 | 9/2013 | Allan et al. | |
| 2013/0253342 A1 | 9/2013 | Griswold et al. | |
| 2013/0253343 A1 | 9/2013 | Waldhauser et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0001044 A1 | 1/2014 | Ecoff et al. | |
| 2014/0005499 A1 | 1/2014 | Catt et al. | |
| 2014/0039383 A1 | 2/2014 | Dobbles et al. | |
| 2014/0052091 A1 | 2/2014 | Dobbles et al. | |
| 2014/0052092 A1 | 2/2014 | Dobbles et al. | |
| 2014/0052722 A1 | 2/2014 | Bertsimas et al. | |
| 2014/0058240 A1 | 2/2014 | Mothilal et al. | |
| 2014/0088393 A1 | 3/2014 | Bernstein et al. | |
| 2014/0266776 A1 | 9/2014 | Miller et al. | |
| 2014/0278189 A1 | 9/2014 | Vanslyke et al. | |

(56) References Cited

U.S. PATENT DOCUMENTS

| | | |
|---|---|---|
| 2014/0350359 A1 | 11/2014 | Tankiewicz et al. |
| 2014/0350369 A1 | 11/2014 | Budiman et al. |
| 2015/0018643 A1 | 1/2015 | Cole et al. |
| 2015/0118658 A1 | 4/2015 | Mayou et al. |
| 2015/0119655 A1 | 4/2015 | Mayou et al. |
| 2015/0120317 A1 | 4/2015 | Mayou et al. |
| 2015/0141770 A1 | 5/2015 | Rastogi et al. |
| 2015/0170504 A1 | 7/2015 | Jooste |
| 2015/0289821 A1 | 10/2015 | Rack-Gomer et al. |
| 2015/0292856 A1 | 10/2015 | Ganton et al. |
| 2016/0029931 A1 | 2/2016 | Salas-Boni et al. |
| 2016/0100807 A1 | 4/2016 | Johnson et al. |
| 2016/0101232 A1 | 4/2016 | Kamath et al. |
| 2016/0103604 A1 | 4/2016 | Johnson et al. |
| 2016/0129182 A1 | 5/2016 | Schuster et al. |
| 2016/0232322 A1 | 8/2016 | Mensinger et al. |
| 2016/0262670 A1 | 9/2016 | Wasson et al. |
| 2016/0321428 A1 | 11/2016 | Rogers |
| 2016/0324463 A1 | 11/2016 | Simpson et al. |
| 2016/0328990 A1 | 11/2016 | Simpson et al. |
| 2016/0331310 A1 | 11/2016 | Kovatchev |
| 2016/0345830 A1 | 12/2016 | Raisoni et al. |
| 2017/0027515 A1 | 2/2017 | Wiser |
| 2017/0157774 A1 | 6/2017 | Pathak et al. |
| 2017/0169358 A1 | 6/2017 | Choi et al. |
| 2017/0172510 A1 | 6/2017 | Homyk et al. |
| 2017/0185748 A1 | 6/2017 | Budiman et al. |
| 2017/0213145 A1 | 7/2017 | Pathak et al. |
| 2017/0215808 A1 | 8/2017 | Shimol et al. |
| 2017/0249445 A1 | 8/2017 | Devries et al. |
| 2017/0273610 A1 | 9/2017 | Suri et al. |
| 2017/0311903 A1 | 11/2017 | Davis et al. |
| 2018/0039097 A1 | 2/2018 | Gutierrez |
| 2018/0103882 A1 | 4/2018 | Biederman et al. |
| 2018/0110078 A1 | 4/2018 | Mandapaka et al. |
| 2018/0125364 A1 | 5/2018 | DeHennis |
| 2018/0256103 A1 | 9/2018 | Cole et al. |
| 2018/0279928 A1 | 10/2018 | Böhm et al. |
| 2019/0075443 A1 | 3/2019 | Fu et al. |
| 2019/0275234 A1 | 9/2019 | Yang |
| 2019/0307958 A1 | 10/2019 | Yang |
| 2019/0328340 A1 | 10/2019 | Yang |
| 2020/0275894 A1 | 9/2020 | Burnette et al. |

OTHER PUBLICATIONS

EP, 18712038.1 Examination Report, dated Oct. 12, 2020.
WO, PCT/US2018/020030 ISR and Written Opinion, dated May 9, 2018.
"Piezoelectric accelerometer" retrieved from https://en.wikipedia.org/wiki/Piezoelectric_accelerometer, pp. 1-4.
Teller, A., "A platform for wearable physiological computing", Interacting with Computers, 2004, vol. 16, pp. 917-937.
Williamson, J., et al., "Data Sensing and Analysis: Challenges for Wearables", The 20th Asia and South Pacific Design Automation Conference, IEEE, 2015, pp. 136-141.

* cited by examiner

METHODS, DEVICES, AND SYSTEMS RELATED TO ANALYTE MONITORING

CROSS-REFERENCE TO RELATED APPLICATIONS

The present application is a continuation of U.S. patent application Ser. No. 17/073,589, filed Oct. 19, 2020, which is a continuation of U.S. patent application Ser. No. 15/868,890, filed Jan. 11, 2018, Now U.S. Pat. No. 10,806,382, which is a continuation of U.S. patent application Ser. No. 14/092,035, filed Nov. 27, 2013, now U.S. Pat. No. 9,872,641, which claims the benefit of U.S. Provisional Application No. 61/731,316, filed Nov. 29, 2012, all of which are incorporated herein by reference in their entirety for all purposes.

BACKGROUND

In many instances it is desirable or necessary to regularly monitor the concentration of particular constituents in a fluid. A number of systems are available that analyze the constituents of bodily fluids such as blood, urine and saliva. Diagnosis and management of subjects (e.g., patients) suffering from diabetes mellitus, a disorder of the pancreas where insufficient production of insulin prevents normal regulation of blood sugar levels, requires carefully monitoring of blood glucose levels on a daily basis.

In vivo analyte monitoring systems include an in vivo positioned analyte sensor. At least a portion of the sensor is positioned beneath the skin surface of a user to contact bodily fluid (e.g., blood or interstitial fluid (ISF)) to monitor one or more analytes in the fluid over a period of time. The sensor remains positioned in the user for a period of time and automatically measures an analyte in the bodily fluid. Data received or otherwise derived from analyte monitoring may be communicated to another device for further processing.

SUMMARY

In some aspects of the present disclosure, the methods, devices, and systems relate to in vivo analyte monitoring devices and systems, and/or communication of data derived therefrom. In vivo analyte monitoring systems include an in vivo positioned analyte sensor. At least a portion of the sensor is positioned beneath the skin surface of a user to contact bodily fluid (e.g., blood or interstitial fluid (ISF)) to monitor one or more analytes in the fluid over a period of time. Data derived from the in vivo analyte sensor may be transferred or otherwise communicated within or between devices—e.g., for logging the data in memory, processing, etc. For example, a system may include an in vivo analyte sensor, a sensor electronics unit that has electrical contacts that electrically and physically connects to the electrical contact(s) of the sensor when the sensor is positioned in vivo (referred to as an on body unit, sensor control unit, and the like), and another (second) electronics device (referred to as an analyte monitoring device, remote, reader, and the like) that communicates with the sensor electronics unit wirelessly. One or both of the sensor electronics unit and/or the (second) electronics device may also communicate wirelessly or with a wire to a PC or other processing device.

In some aspects, the system is configurable to switch between a plurality of different modes or configurations, in many instances automatically (i.e., passively) without user intervention. For example, the second electronics device may be a universal reader that can be configured for a variety of different uses or modes. Configuration may be accomplished simply by pairing the universal reader to the on body unit. This may include transferring configuration information or instructions between the on body unit and the universal reader, in many instances without the user doing anything other than pairing (e.g., initiating the pairing by bringing the devices in appropriate proximity to each other or other pairing action).

In some aspects of the present disclosure, methods, devices, and systems are provided that enable configuration settings (e.g., related to user interface features, or other device settings) of the second electronics device to be settable by the on body unit and the particular desired use of the on body unit. The on body electronics unit can switch between at least two different settings or uses, and the given setting can be determined by the on body unit and communicated to the second electronics device. For example, in one embodiment, one type of use provides for the second electronics device to be configured to operate in a masked mode (e.g., a mode where the analyte levels are not displayed or otherwise communicated on the display of the second electronics device for the subject to view or otherwise receive), and a second type of use provides for the second electronics unit to be configured to operate in an unmasked mode (e.g., a mode where the analyte levels are displayed or otherwise communicated on the display of the second electronics device for the subject to view or otherwise receive). In general, the masked mode of operation is particularly useful during clinical use (e.g., collecting analyte levels for a period of time for subsequent analysis by a clinical professional, such as a doctor, for purposes of diagnosis and/or analysis of development of disease condition, such as diabetes) of the analyte sensor while the unmasked more of operation is particularly useful during personal use of the analyte sensor (e.g., routine, such as daily, monitoring of analyte levels by a user for purposes of controlling a disease condition, such as monitoring of glucose levels by a diabetic user and optionally administering insulin in response to detected glucose levels). The clinical sensor and the personal use sensor may also include other configuration settings that differ, in addition to or instead of masked mode and unmasked mode.

In some aspects of the present disclosure, methods, devices, and systems are provided that sample analyte levels more frequently than they are logged or otherwise recorded in memory. For example, analyte levels derived from an in vivo positioned analyte sensor may be recorded at longer recording intervals than the maximum sampling intervals of the system (or recorded at a slower recording frequency than the minimum sampling frequency of the system). If a sampled analyte level to be recorded is missing or contains data that is determined to be not valid, then an alternative sampled analyte level (e.g., a neighboring sampled analyte level) may be recorded instead if valid—e.g., with an appropriate adjustment to the timestamp of the record. Multiple alternative samples may be selected until a valid sample is found, or until a predetermined time to stop is reached.

In some aspects of the present disclosure, methods, devices, and systems are provided that enable an on body unit (e.g., that includes an in-vivo positioned analyte sensor and sensor electronics coupled to the in-vivo positioned analyte sensor) to dynamically adjust the data logging frequency independent of instructions from a second electronics device. For example, in one embodiment, analyte levels are monitored at one frequency and logged or otherwise recorded in memory at a variable frequency—e.g., to track the history of the analyte levels. The variable frequency is adjustable based on the monitored data, and is adjustable to slower frequencies than the frequency at which the monitored data is obtained. Adjusting can be automatic and in real time.

In some aspects of the present disclosure, methods, devices, and systems are provided that enable an on body unit (e.g., that includes an in-vivo positioned analyte sensor and sensor electronics coupled to the in-vivo positioned analyte sensor) to dynamically adjust the data logging frequency based upon communications with a second electronics device, such as analyte monitoring device. The second electronics device may communicate frequency-adjusting information to the on body unit that is then used to determine whether to adjust the variable frequency of the recorded data. The communication of the information and/or the adjustments of the recording frequency may occur at discrete times or otherwise be performed dynamically in real-time, automatically, for example.

In some aspects of the present disclosure, methods, devices, and systems are provided that provide for monitoring analyte levels with an in-vivo positioned analyte sensors by acquiring or storing analyte levels from the in-vivo positioned analyte sensor at randomly determined periods of time.

In some aspects of the present disclosure, methods, devices, and systems are provided that enable the configuration of recording parameters as the system is being used or otherwise operated. The recording parameters may include, for example, the recording duration (e.g., the duration of time that data points should be sampled and stored), the recording rate (e.g., the intervals between recorded samples), etc. For example, a system designer and/or a user (e.g., a physician, health care provider, patient, etc.) may configure the recording parameters as the system is operable, for example at least until manufacturing time. In this way, for example, on body unit may be designed with a modest amount of memory and the system designer and/or user may make the best use of the available memory already implemented in the device.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol used in one drawing to refer to a particular element may be used in another drawing to refer to a like element.

DETAILED DESCRIPTION

Figure 1:
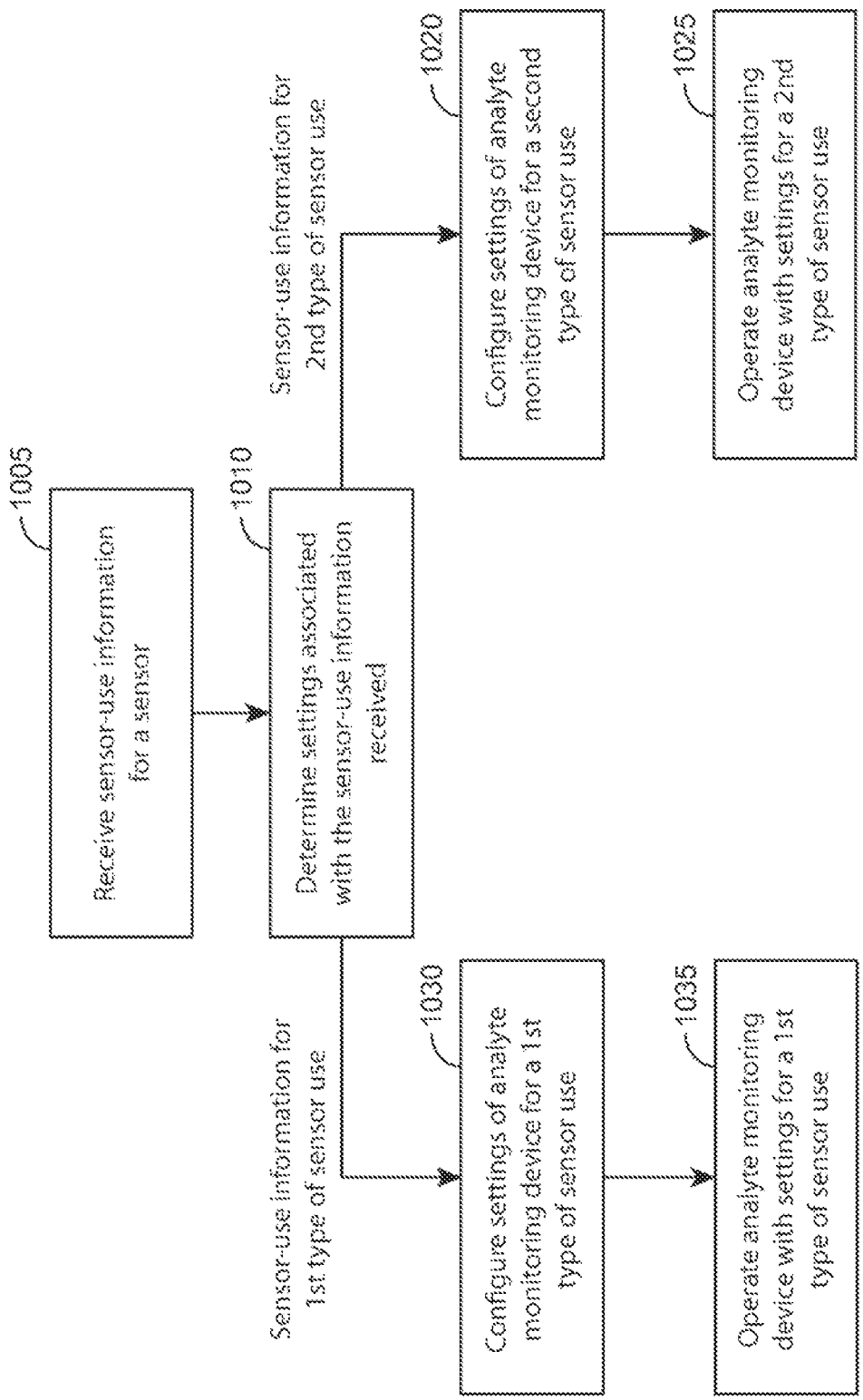
FIG. 1 illustrates a flowchart for configuring and operating an analyte monitoring device with analyte sensing device of different uses, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

The term "processor" is used broadly herein, and may include any type of programmable or non-programmable processing device, such as a microprocessor, microcontroller, application-specific integrated circuits (ASICS), programmable logic devices (PLDs), field-programmable gate arrays (FPGAs), etc. The term "processor" may also include multiple processing devices working in conjunction with one another.

Configuring Settings Based on Use of an Analyte Sensor:

Embodiments of the present disclosure includes a transcutaneously positionable analyte sensor in signal communication with electronics which process signals from the analyte sensor transfer or otherwise provide the processed signals related to monitored analyte level to a receiver unit, a blood glucose meter or other devices configured to receive, process, analyze, output, display and/or store the processed signals. Embodiments of the analyte monitoring systems include in vivo analyte sensors in fluid contact with body fluid such as interstitial fluid to monitor the analyte level such as glucose. Embodiments include electronics and/or data processing, storage and/or communication components that are electrically coupled to the analyte sensor, and may include a housing that is placed or positioned on the body surface such as on the skin surface and adhered thereon with an adhesive and retained and maintained in the adhered position for the duration of the analyte monitoring time period using the analyte sensor such as, for example, about 15 days or more, about 10 days or more, about 7 days or more, or about 5 days or more, or about 3 days or more. The housing including the electronics and/or data processing, storage and/or data communication components may be positioned on discrete on-body locations including under clothing during the duration of the monitoring time period. The analyte monitoring device that is coupled to the body and includes the transcutaneously positionable analyte sensor, housing, and electronics and/or data processing, storage and/or communication components, is also referred to herein as an "on-body unit", "obu", "on body patch", or "patch".

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

When positioned on the skin of a patient, the sensor and the electronic components within the sensor control unit are coupled via conductive contacts. The one or more working electrodes, counter electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

The sensor control unit also typically includes at least a portion of the electronic components that measure the sensor current and the analyte monitoring device system. The electronic components of the sensor control unit typically include a power supply for operating the sensor control unit, a sensor circuit for obtaining signals from the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

In vivo analyte monitoring devices and system may include an on body unit having sensor electronics and an analyte sensor whereby at least a portion of the sensor is positioned beneath the skin surface of a user to contact bodily fluid (e.g., blood or interstitial fluid (ISF)) to monitor one or more analytes in the fluid over a period of time. In some embodiments, the analyte levels are communicated to a second electronics device, such as an analyte monitoring device, which remains in constant (e.g., continual, continuous) signal communication range with the on body unit thereby transferring the analyte levels to the analyte monitoring device at continuous or near continual rate.

In other embodiments, the analyte levels are communicated to second electronics device, such as an analyte monitoring device, only when the analyte monitoring device is brought into signal communication range with the on body unit. For example, the signal communication can be configured for only near field communication, such as, for example, through RFID protocol and the like. Such an exemplary in vivo measuring embodiment provides for collection of analyte data from the on body sensor upon demand (i.e., flash) by the user upon bringing the analyte monitoring device in close proximity to the on body unit such that they are in signal communication with one another to transfer the analyte information and then taken out of signal communication range of one another. In addition, such embodiments are optionally also configured to provide for no user calibration of the analyte levels derived from the in vivo sensor by using, for example, blood glucose derived analyte levels (e.g., capillary blood from a finger, arm, palm, etc.) using an in vitro blood glucose test strip and meter.

In some aspects of the present disclosure, the configuration settings (e.g., related to user interface features or settings) of the analyte monitoring device are determined by the on body unit and/or its use. In some embodiments, the analyte monitoring device is configurable to operate with on body units of different uses (e.g., masked or blinded display uses, and unmasked or unblinded display uses), which have different analyte monitoring device settings (e.g., user interface settings) associated with them. Example settings may include, but are not limited to: display settings (e.g., whether to display analyte levels on the display of the reader); data sampling and/or logging frequency settings (e.g., 5 hours of 10 minute data, 8 hours of 15 minute data, 24 hours of 45 minute data, etc.); settings for the life of the sensor (e.g., 7 days, 14 days, etc.), user interface settings (e.g., reminders, statistics, activation of bolus calculator, or other features associated with visual representation of when the sensor analyte values may be accurate enough to enable treatment decisions; report settings, either printed, displayed, or both (e.g., specific reports may be enabled, prioritized, etc. for the corresponding application), etc. These settings may vary depending on the specific use of the on body unit. The settings described are exemplary, and other settings may be applicable in other embodiments.

In one embodiment, the analyte monitoring device is configured based on sensor-use information that is received from the on body unit. The sensor-use information indicates the type of use that the sensor is configured for—e.g., a first use such as masked or blinded (clinical use) and at least a second use such as unmasked or unblinded (personal use). The sensor-use information may be stored in memory of the on body unit and communicated to the analyte monitoring device upon initial signal communication between the two, for example, such as initialization of the system. Based on the type of use indicated by the sensor-use information, the analyte monitoring device is configured accordingly for the indicated use. In one embodiment, the analyte monitoring device is automatically configured by the on body unit. In another embodiment, at least user confirmation of the configuration is requested by one of the system components, and may not proceed with one or more functions until received. In some embodiments, the user may be required to perform some other action on one or more of the first and second devices such as actively selecting a particular setting from amongst a plurality of available settings. This may be included on a user inter face of one or more of the devices of a system. Accordingly, configuration may be semi-automatic or less.

The sensor-use information may include, for example, identification information for the on body unit that may be unique to each device, such as a unique identification (UID), a programmed flag or some other information stored on the on body unit to indicate the desired use. The analyte monitoring device may include information stored in memory, for example, that identifies or otherwise associates each sensor-use information with its corresponding use, and further with the associated settings for the corresponding use. The analyte monitoring device may use the stored information to determine the associated use (e.g., masked or unmasked) and then initiate the configuration of the analyte monitoring device with the associated settings. For example, in one embodiment, the unmasked use sensor differs from the masked use sensor in that the unmasked use sensor displays analyte values to the user via the display on the analyte monitoring device and the masked does not.

For example, a physician or health care provider may provide a subject (e.g., patient) with an analyte monitoring device and on body unit configured for masked (clinical) use. For instance, the subject may be a diabetic subject and the glucose sensing device provided in order to obtain a baseline or other view of the subject's glycemic control. At this time, the analyte monitoring device is configured with settings for the masked version of the on body unit—e.g., operating in a clinical mode that does not display glucose values to the user, etc. Upon communication between the clinical use on body unit and the analyte monitoring device (e.g., upon activating the clinical use sensing device, or upon performance of a glucose reading if applicable, etc.), the sensor-use information that is stored on the clinical use on body unit communicated to the analyte monitoring device, for example wirelessly by an RF communication protocol such as RFID or the like. Sensor-use information (e.g., sensor unique ID, etc.) indicates to the analyte monitoring device that the on body unit is a clinical use sensor, and the analyte monitoring device is configured accordingly for the clinical use settings.

After the subject is finished with the clinical use version of the on body unit, the same analyte monitoring device may be used as a monitor with a different on body unit configured for a different use (e.g., personal use) to monitor glucose levels. An on body unit for unmasked (personal use) may be obtained, and replace the first masked unit. Upon communication between the unmasked on body unit and the currently configured masked analyte monitoring device (e.g., upon activating the personal use sensor, or upon performance of a reading, etc.), the sensor-use information that is stored on the new or second unmasked use on body unit is communicated to the currently configured masked analyte monitoring device. The sensor-use information (e.g., sensor UID, etc.) indicates to the analyte monitoring device that the on body unit is an unmasked device, and the analyte monitoring device is then configured accordingly to a second or unmasked state to match the masked state of the on body unit in current use (e.g., in an unmasked mode that displays analyte values to the user).

In one embodiment, the sensor-use information may distinguish between different types of on body units that are configured for personal use but that have their own specific settings associated with them. These settings may differ, for example, based on the differences in various sensors—e.g., differences in models of the sensors, differences in the firmware or software of the sensors, etc. In some instances, prices for the unmasked use on body units and the masked use on body units may then be decoupled and based upon the features that are unlocked with their respective use. Accordingly, based on the personal use on body unit paired with the analyte monitoring device, all features of the monitoring device may be activated, or certain features may be activated, while others may be deactivated. Such activating and deactivated features may include accessibility to logbook features, flagging of analyte values as pre- or post-meal, data analysis such as deriving analyte level pattern information from analyte values over a period of days, etc. Furthermore, in the sensor-use information may distinguish between a battery operated on body unit and a self-powered on body unit as described in U.S. Patent Application Publication No. 2010/0213057, the subject matter of which is incorporated herein by reference in its entirety. In such embodiments, when a self-powered on body unit is used the analyte monitoring device may be configured to receive trend information from resistor pairs as described in U.S. Patent Application Publication No. 2011/0257495, the subject matter of which is incorporated herein by reference in its entirety.

In other embodiments, configuration of the analyte monitoring device may also be done, for example, via other passive approaches such as bar coding (e.g., on the on body unit, inserter, and/or product labeling), user entry of a key code, and/or through the reader user interface.

FIG. 1 illustrates a flowchart for configuring and operating an analyte monitoring device with on body unit of different uses, according to one embodiment. At block 1005, when the analyte monitoring device and the on body unit are communicably coupled, sensor-use information stored in the on body unit is received by the analyte monitoring device.

At block 1010, the analyte monitoring device determines configuration settings associated with the sensor-use information. For example, the analyte monitoring device may have specific configuration settings for each of the different types of sensor-uses, which is indicated by the sensor-use information. The analyte monitoring device may include memory that contains data that associates the specific sensor-use information with their corresponding configuration settings for the analyte monitoring device (e.g., stored in a look-up table in memory of the analyte monitoring device). In another embodiment, the sensor-use information includes the information for the associated settings and provides the configuration settings to the analyte monitoring device.

If the sensor-use information is associated with a first type of sensor-use (e.g., clinical use), then the analyte monitoring device is configured with settings for the first type of sensor-use and then operated with those settings, as represented by block 1030 and 1035, respectively. Alternatively, if the sensor-use information is associated with a second type of sensor-use (e.g., personal use), then the analyte monitoring device is configured with settings for the second type of sensor-use and then operated with those settings, as represented by block 1020 and 1025, respectively.

The first type of sensor-use (e.g., clinical) and second type of sensor-use (e.g., personal) may include one or more different settings. In some embodiments, there may be more than two types of sensor-use. The types of sensor-use may have different configuration settings associated with them, such as one or more of the following: analyte level display settings, such as whether to display analyte levels on the display of the reader; data sampling and/or logging frequency settings; settings for the life of the sensor, the analyte monitoring device's user interface settings (e.g., reminders, statistics, activation of bolus calculator, or other features associated with visual representation of when the sensor glucose values may be accurate enough to enable treatment decisions); report settings, either printed, displayed, or both (e.g., specific reports may be enabled, prioritized, etc. for the corresponding application), etc.

In one embodiment, one type of on body unit is clinical use and the other type of on body unit is personal use, where in clinical use the analyte monitoring device is configured to operate in a masked mode (e.g., a mode where the analyte levels are not displayed on the display of the analyte monitoring device for the subject to view), and in personal use, the analyte monitoring device is configured to operate in an unmasked mode, e.g., a mode where the analyte levels are displayed on the display of the analyte monitoring device for the subject to view. The clinical sensor and the personal use sensor may also include other configuration settings that differ, in addition to masked mode and unmasked mode.

Selective Data Logging:

Analyte levels acquired by analyte sensors at a constant recording frequency (e.g., every 10 minutes) are affected by noisy or otherwise inaccurate data, such as transient signals for instance. When the recording frequency is low, transient signal faults that coincide with scheduled recording times may significantly impact the quality of the recorded data. For example, if a normal signal contains an unwanted disturbance at time t that lasts for one minute, a system with a one-minute recording frequency would log one time point of faulty data, bracketed by normal ("valid") data points both one minute before and one minute after time t. In this case, the signal disturbance causes a two-minute gap between valid data points in the log. However, if the same signal is recorded at longer intervals such as ten minute intervals, and a recording is made at time t, then the gap between valid data points in the log is much larger—e.g., 20 minutes. Low recording frequency can significantly compromise signal processing algorithms (e.g., interpolation between valid logged data points) when transient signal disturbances are present.

In some aspects of the present disclosure, methods, devices, and systems are provided that sample analyte levels more frequently than they are logged or otherwise recorded in memory. For example, analyte levels derived from an in vivo positioned analyte sensor may be recorded at longer intervals than the maximum sampling intervals of the system (or recorded at a slower recording frequency than the minimum sampling frequency of the system). If a sampled analyte level to be recorded is missing or contains data that is determined to be not valid, then an alternative sampled analyte level (e.g., a neighboring sampled analyte level) may be recorded instead if valid—e.g., with an appropriate adjustment to the timestamp of the record. In this way, the selectively data logging may improve the data inputs available for signal processing and increase the robustness of the sensing system to transient signal faults. Furthermore, slower recording frequencies may benefit data storage and data transfer limitations of low cost sensing systems.

The sampling of analyte levels refers generally herein to the analyte levels obtained from the in-vivo positioned sensor. The recording or logging of the analyte levels refer generally to the storing of analyte levels to memory. The recorded analyte levels may then, for example, be used by signal processing algorithms in the processor of the device or another device.

In some instances, a valid alternative analyte level may not be found. For example, limits may be placed on how far in to the past and future the data logging algorithm will look for a valid alternative sample to record if the sample at a scheduled recording time point is invalid. In cases where no valid alternative sample can be found, predetermined criteria may be used to determine what analyte level is to be recorded, whether no record should be recorded in such case, etc.

The term "valid" is used herein to refer generally to whether a data point is determined to be worth recording, or a level of worthiness for recording. Any variety of algorithms may be implemented and may utilize various factors and considerations; however, the algorithms should ultimately provide a validity determination for a give data point. In some embodiments, the validity of a data point may be binary (e.g., either valid or invalid). A valid data point would be considered acceptable to record and an invalid data point would be considered unacceptable to record (e.g., a missing analyte level, significantly unstable or corrupted analyte level (e.g., by noise or transient signal faults, etc.). In other embodiments, the validity of a data point may not be binary but rather be a level of validity. For example, various levels of validity may be implemented to reflect a data point's worthiness of being recorded—e.g., as based on a data point's level of stability, degree of accuracy, or degree of corruption; or on a data point's likelihood of being stable, accurate, or uncorrupted; etc. Absent analyte levels would have a low, if not lowest level of validity, for instance.

In some aspects, the methods, devices, and systems relate to devices and systems including an in-vivo positioned analyte sensor that may be configured so that at least a portion thereof is placed under the skin of the subject to detect the analyte levels of the subject, and another portion of the analyte sensor—which may be above the skin—is coupled to electronics within a housing that is positioned externally on the skin of the subject. The sensor electronics may include various components, such as communication element(s) for communication with a remote receiving unit; a processor; memory; etc.

The terms "on body unit" and "analyte sensing device" are used herein to generally refer to the entire sensing device including the in-vivo positionable analyte sensor, sensor electronics coupled to the in-vivo positionable sensor (e.g., data processing, storage, and/or communication components), and housing which couples to the subject's body. The analyte sensing device is configured to communicate (e.g., wired or wirelessly) with an analyte monitoring device and send analyte data to the analyte monitoring device. The analyte monitoring device may be, for example, an any variety of hand-held measurement instruments or analysis instruments, such as a remote or reader for instance. The analyte monitoring device may also be another data processing device such as a personal computer, laptop, cell phone or smartphone, personal digital assistant (PDA), etc. For example, glucose samples may be sampled from an in vivo positioned glucose sensor by the sensor electronics coupled to the in-vivo positioned glucose sensor, and recorded in memory of the sensor electronics at longer intervals than the maximum sampling interval. The recorded glucose levels may then be sent to a receiving unit, such as a glucose monitoring device.

In one embodiment, for example, data is recorded at intervals of $T_R$ and sampled at intervals of $T_S$, which is a multiple of $T_R$. If a recording is scheduled at time t, and the sample at time t is invalid, wait until time $t+T_S$ to sample. If the sample is valid, then record the sample. If it is not valid, then wait to sample at $t+2\ T_S$, $t+3\ T_S$, ..., $t+nT_S$, stopping when a valid record is found. In one embodiment, $nT_S$ should not exceed $T_R$, and n should not exceed a predefined $n_{max}$. The algorithm is not confined to start at time t, and may start as early as $t-n_{max}T_S$, and stop as soon as it reaches the first valid point, for example. A recording window may be used herein to refer generally an interval of time defined by the recording time points immediately prior to and immediately subsequent to a given recording time point. For instance, in the example provided, the time interval between $t-n_{max}T_S$ and $t+n_{max}T_S$ may be referred to as the recording window.

In some embodiments, if the validity of a sample is not a binary (e.g., valid or invalid) metric but a continuous or discrete value (e.g., signal stability levels, where 0 is completely unstable and 10 is perfectly stable), the selective data logging algorithm may weigh the validity of the sample (e.g., against its deviation from the scheduled recording time), so that an optimal sample can be recorded for instance. In one embodiment, for example, a penalty function may be defined as a function of $\Delta t$, where $\Delta t$ is the difference between the scheduled recording time and any given alternative recording time. The output of the penalty function may be combined with the validity metric of a given alternative recording time to score the samples and identify the optimal sample to record in the data log, for instance.

The methods, devices, and systems may be implemented with or without a sample buffer. For example, multiple samples may be stored in a temporary data buffer, and all samples in the buffer may be evaluated to determine the optimal sample to record. In the absence of a buffer, for example, the data logging algorithm may start by recording the $n_{max}^{th}$ sample before time t. If the next sample has a better validity score, then it will replace the existing record with the most recent sample. For instance, the algorithm may only replace the current record if it finds a sample with a better validity score.

Rather than replacing data records with more valid sample data, in some embodiments, the method may combine data from multiple samples to produce the values stored in the data record. For example, if all the samples in the recording window do not meet the validity criteria for recording, the median of all the sample values (or any subset thereof) may be recorded rather than recording no value at all.

The method, devices and systems, may not be limited to data logging of a single channel of data, and may include multi-channel data where transient signal faults may occur along any (or all) of the data channels. In the case of multi-channel data, the validity scoring functions may depend on several input channels, for example. In some instances, the scoring functions may be defined differently for each channel. In some instances, the optimal record that is ultimately logged may contain channel data that is not necessarily form the same time point, so that signal faults in any signal channel do not prevent a complete record from being logged and used in downstream signal processing.

In some embodiments, the value of "n" may be recorded along with each data sample. In this way, for example, it may be indicated to subsequent signal processing routines (in the same or different device) whether the data time was altered, to what degree that the data timing was altered, etc. For example, for a ten minute sample, if $n_{max}$ is 5, then 4 additional bits (enough to represent 11 possibilities) may be recorded per data sample. The signal processing routine may use this information along with standard interpolation techniques, for example, to estimate what the value at the regular sample spacing time is.

Figure 2:
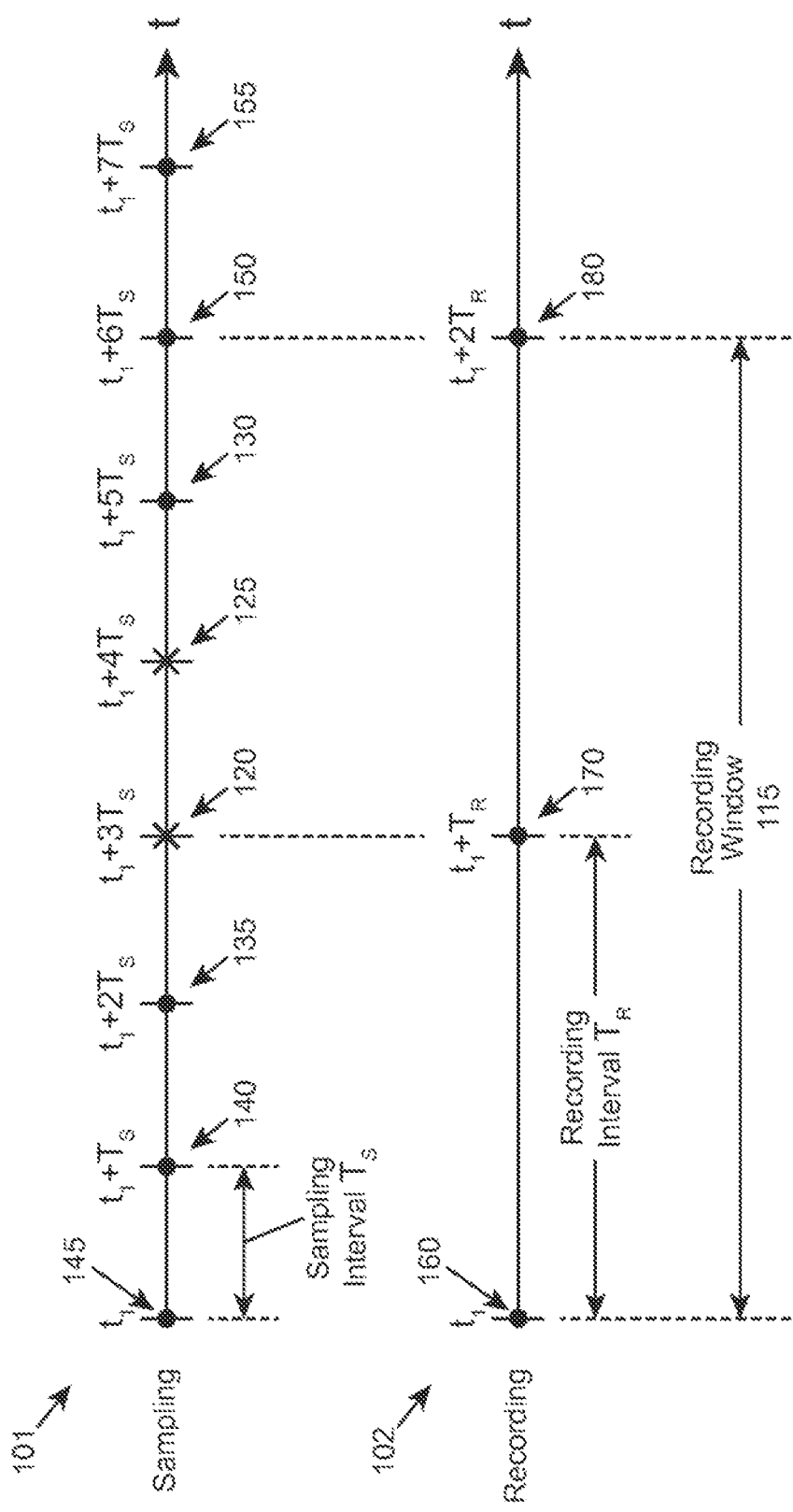
FIG. 2 illustrates a time plot of the sampling and recording of analyte level data, according to one embodiment.

FIG. 2 illustrates a time plot of the sampling and recording of analyte level data, according to one embodiment. Plot 101 shows sampling intervals represented by time points along a timeline. The time points define intervals of $T_S$, also referred to as the sampling interval. The sampling of analyte levels occurs at sampling intervals $T_S$, beginning at time point $T_1$. For example, at time point $t_1$, an in-vivo positioned sensor is sampled and an analyte level obtained, as represented by the data point 145 at $t_1$. After the sampling interval of TS, another analyte level is obtained, as represented by the data point 140 at time point t1+TS. After another sampling interval, another analyte level is obtained, as represented by the data point 135 at time point t1+2TS. Similar data points 130, 150, 155 are shown at corresponding time points t1+5TS, t1+6TS, t1+7 $T_S$, respectively. Data points 120, 125 are shown as a letter "X" at time points t1+3TS and t1+4TS, respectively, and represent data points with validity concerns—e.g., missing data, invalid data (e.g., unstable values, corrupted values from noisy or transient signal faults, outliers values, dropouts values, etc.), or data that is otherwise unlikely to be valid or considered to have a low validity level.

Plot 102 shows recording intervals defined by recording time points along a timeline. The time points occur at intervals of TR, also referred to as the recording interval. The recording of sampled analyte levels are shown to occur at the recording interval TR, beginning at time point T1. For example, analyte levels are recorded as shown by the data points 160, 170, 180 at time points t1, t1+TR, T1+2TR, respectively. In the embodiment shown, the recording interval $T_R$ is a multiple of $T_S$—more specifically, $T_R$ is three times the size of $T_S$. In other embodiments, recording interval $T_R$ may be include more than one sampling interval $T_S$. In some instances, $T_R$ may be another multiple of $T_S$. Also shown is recording window 115, which is a time interval defined by the recording time points t1 and t1+2TR that are immediately prior to and immediately subsequent to time point t1+TR, respectively.

The value of the analyte levels recorded for each recording interval are determined based on validity determinations performed on one or more of the sampled analyte levels, which will be discussed in further detail in FIGS. 2 and 3.

Figure 3:
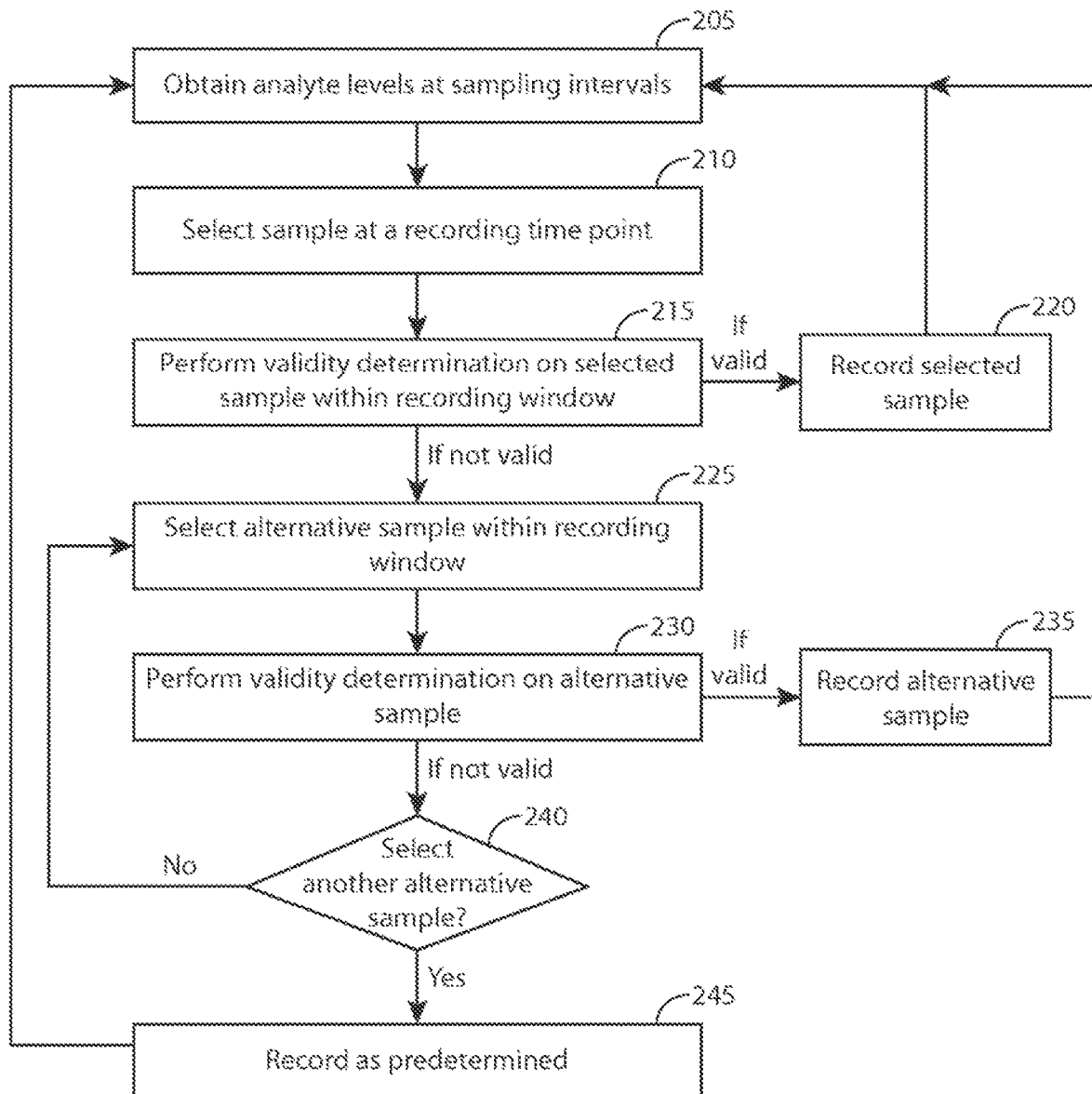
FIG. 3 illustrates a flowchart for sampling and recording analyte levels, according to one embodiment.

FIG. 3 illustrates a flowchart for sampling and recording analyte levels, according to one embodiment. At block 205, analyte levels are sampled at sampling intervals. For example, an analyte sensor may be coupled to sensor electronics and positioned in-vivo in a subject. The analyte sensor may be activated and begin sampling analyte levels at sampling intervals. For example, at each sampling time point of the sampling intervals, an analyte level is obtained or attempted to be obtained. In some case, a valid analyte level is obtained and at other times an invalid or otherwise inaccurate analyte level may be obtained instead. For example, an analyte level may not be present or may not be sufficiently valid for recording (e.g., due to signal noise or disturbances, transient signals faults, signal outliers, signal dropouts, etc.).

The sampled analyte levels are initially set to be recorded at recording intervals which are larger than the sampling intervals (e.g., to include more than one sampling interval, such multiple sampling intervals). At block 210, a sampled analyte level at a time point of a recording interval is selected, and at block 215 a validity determination is performed on the selected sample. The sample initially selected for recording is the sampled analyte level coinciding with the next recording time point. For example, referring back to FIG. 1, at time point t1, the sampled analyte level 145 is selected. Instead of being recorded, sampled analyte level 145 is subjected to a validity determination to determine if it is a valid data point. Any variety of validity determination algorithms may be implemented to determine if the analyte level is a valid analyte level.

If the analyte level is determined to be valid, then the selected analyte level is recorded, as represented by block 220, and the process repeated for the next recording time point, as represented by the arrow from block 220 back to block 205. If the analyte level is determined to be invalid, then an alternative sampled analyte level is selected and a validity determination performed on the alternative analyte level, as represented by blocks 225 and 230, respectively. In the embodiment shown, the alternative sampled analyte level is selected from within the recording window of the initially selected sample that was determined to be invalid. For example, referring back to the example for FIG. 1, after analyte level 145 was recorded for time point t1, the analyte level sampled at the next recording time point t1+TR is selected. The sampled analyte level coinciding with the recording time point t1+TR is shown as data point 120. Data point 120 represents a missing or invalid data point, and thus when data point 120 is selected at block and a validity determination is performed, an invalid determination results. In such case, an alternative sampled analyte level is selected, as represented by block 225.

If the validity determination of the alternative sampled analyte level is valid, then the alternative sampled analyte level is recorded instead of the initially selected sampled analyte level at block 210. The process is then repeated for the next recording time point, as represented by the arrow from block 235 back to block 205.

For example, if sampled analyte level 135 is selected at block 225 as the alternative sample, then a validity determination is performed on analyte level 135 at block 230. As sampled analyte level 135 is shown as a valid data point, the validity determination results in a valid data point and then the sampled analyte level 135 is recorded at recording time point t1+TR, in place of data point 120 which was determined to be invalid, as represented by block 235.

If the validity determination of the alternative sampled analyte level is invalid, then another alternative sampled analyte level may be selected (if permitted) and a validity determination performed on the alternative analyte level, as represented by the flow path from block 230 back to block 225). In the embodiment shown in FIG. 2, at block 240, it is determined whether another alternative sampled analyte level should be selected.

If, for example, the alternative analyte level selected at block 225 was sampled analyte level 125, then a validity determination is performed on the analyte level 125 at block 230. As sampled analyte level 125 is shown as an invalid data point, the validity determination results in an invalid data point. If it is determined at block 240, that another alternative sample should be selected, then another alternative sampled analyte level is selected for validity determination, as represented by the arrow from block 240 back to block 225.

For example, the device or system may be programmed to stop selecting alternative analyte levels for validity determination according to predetermined criteria—e.g., after a predetermined threshold number of alternative analyte levels (e.g., after 1 alternative analyte level, or 2 alternative analyte levels, or 3 alternative analyte levels, etc.), etc. If, for instance, an invalid determination is found at block 230, then it is determined if the last threshold alternative analyte level has been selected and tested for validity, as represented by block 240. If the last threshold alternative analyte level has not been selected yet, then another alternative analyte level is selected, as represented by the arrow back to block 225. In one embodiment, the system is programmed to stop selecting alternative analyte levels before reaching the sampled analyte level at the end of the recording window (e.g., the sampled analyte level coinciding with the previous and/or next recording time point). For example, for recording time point t1+TR, the end of the recording window 115 resides at recording time points t1 and t+2TR. In such case, depending on the order of selection, the system would be programmed to stop selecting alternative analyte levels before reaching the sampled analyte levels coinciding at either time point t1 or time point t1+6TS, which may be more applicable to the recordings for time points t1 and t1+6TS than the recording at time point t1+TR.

If the last threshold alternative analyte level has already been selected and determined to not be valid, then at block 245 an appropriate measure is taken as predetermined. For example, it may be predetermined to record no analyte level for the corresponding recording time point. Alternatively, the device or system may be programmed to record a representative analyte level. For instance, the system may select one of the selected sampled analyte levels that is determined to be closest to a valid data point, may average or weight two or more sampled analyte levels at the recording time point (e.g., two or more of the samples in the corresponding recording window), may calculate or otherwise generate another representative analyte level, etc. After block 245, the process is continued to determine the analyte level to be recorded at the next recording time point.

The order of selection of alternative analyte levels may vary in different embodiments. For example, in one embodiment, each successively selected alternative analyte level is the sample at the next subsequent sampling time point—e.g., from time point t1+3TS in FIG. 1, the first alternative analyte level occurs at the next subsequent sampling time point of t1+4TS, the second alternative analyte level occurs at the next subsequent sampling time point t1+5TS, etc. In another embodiment, for example, each successively selected alternative analyte level is the sample at the previous sampling time point (e.g., from time point t1+3TS in FIG. 1, the first alternative analyte level occurs at the previous sampling time point of t1+2TS, the second alternative analyte level (if it were invalid) would occur at the previous sampling time point t1+1TS, etc. In yet another embodiment, for example, the device or system may be programmed to select alternative analyte levels based on distance from the recording time point—e.g., from time point t1+3TS in FIG. 1, alternative analyte levels at time points t1+2TS and t1+4S would be selected (in either order) before analyte levels at time points t1+2T1 and t1+5TS, etc. In yet other embodiments, other permutations may be implemented for the order of selection of alternative analyte levels.

In some embodiments, the analyte levels are recorded in memory along with adjusted time stamps for alternative analyte levels that were recorded. For example, referring to FIG. 1, if the sampled analyte level 130 at sampling time point t1+5TS is used for recording time point t1+TR, then an adjusted time stamp (e.g., t1+5TS) is also recorded with the analyte level 130 to reflect the time of the alternative analyte level 130.

Figure 4:
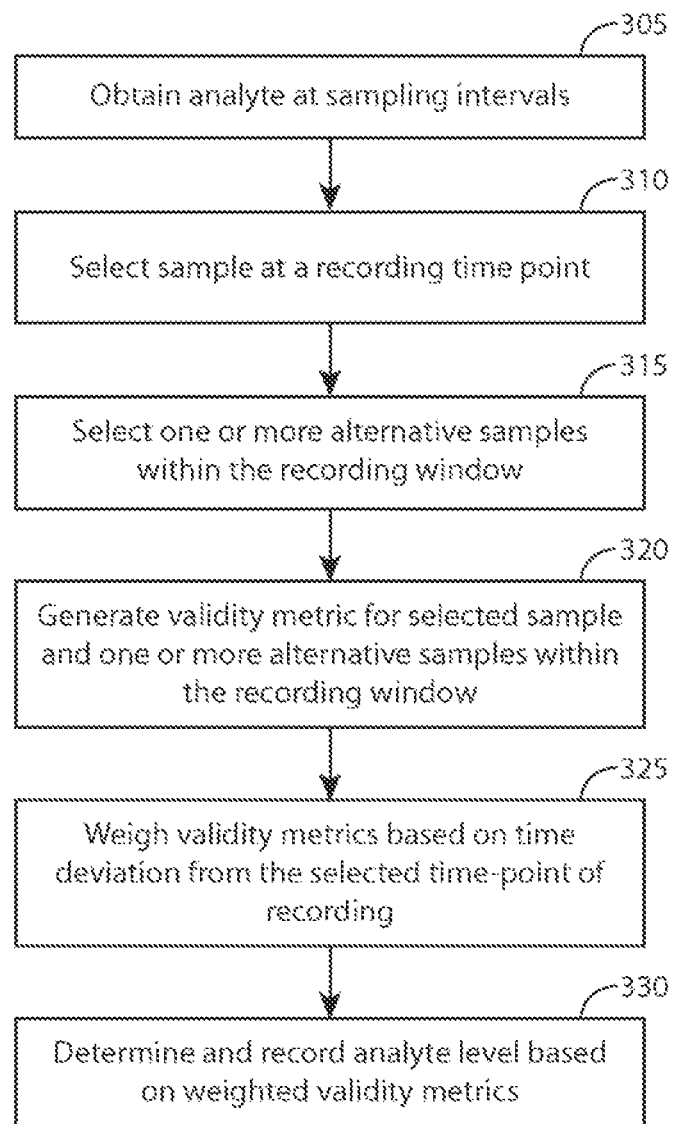
FIG. 4 illustrates a flowchart for sampling and recording analyte levels, according to one embodiment.

FIG. 4 illustrates a flowchart for sampling and recording analyte levels, according to one embodiment. At block 305, analyte levels are sampled at sampling intervals. At each sampling time point of the sampling intervals, an analyte level is obtained or attempted to be obtained. Again, in some cases, a valid analyte level is obtained and at other times an invalid analyte level may be obtained instead.

At block 310, a sampled analyte level coinciding with a recording time point is selected. At block 315, one or more alternative samples within the recording window for the recording time point is selected. For example, in one embodiment, two sampled analyte levels may be selected (e.g., the analyte level coinciding with the current recording time point and the next subsequent sampled analyte level). In another embodiment, for example, three sampled analyte levels may be selected (e.g., the analyte level coinciding with the current recording time point, and the immediately preceding and following sampled analyte levels from the current recording time point). Any variety of combinations of sampled analyte levels in the recording window may be implemented in other embodiments.

At block 320, validity metrics are calculated for the sampled analyte level coinciding at the recording time point and for the one or more alternative sampled analyte levels that were selected at blocks 310 and 320. The calculated validity metric may be a number or value used to represent the degree, level, or score of validity for an analyte level, as determined by any variety of validity determination algorithms. For example, the validity metric may be a level from 1 to 5, where 1 represents the least amount of assurance of validity and where 5 represents the highest assurance of validity. In other embodiments, other scales or numbering systems may be implemented—e.g., 1 to 10; low, medium, high; etc. In this way, the validity determination may include levels of validity as opposed to a binary (valid or invalid) determination.

At block 325, the validity metrics are weighed based on their time deviation from the recording time point from block 310. For example, in one embodiment, validity metrics associated with greater deviations from the recording time point from block 310 are given less weight than validity metrics that have smaller deviations from the recording time point. In this way, the resulting weighted validity metric is a product of both the validity metric (e.g., the level of validity) and the weighting (e.g., the deviation from the recording time point), and account for both factors.

At block 330, an analyte level for recording is determined based on the weighted validity metrics for the selected analyte levels. For example, in one embodiment, the resulting weighted validity metric with the most optimum value for validity determines which analyte level is selected for recording. The process is then repeated as represented by the arrow back to block 305.

In another embodiment, the validity metric may be used without being weighted (e.g., as shown in block 320), and the sampled analyte level with the most optimum validity metric determines which analyte level is recorded. In other embodiments, other factors may also be used in combination with the weighted validity metric (or the non-weighted validity metric) to determine which analyte level is to be recorded. In other embodiments, the weighted validity metrics (or non-weighted validity metrics) are used to calculate or generate a representative analyte level for the recording time point.

Adjustable Logging Frequency:

In some aspects, methods, devices, and systems are provided that enable an on body unit (e.g., including an in-vivo positioned analyte sensor and sensor electronics coupled to the in-vivo positioned analyte sensor) to dynamically adjust the data logging frequency independent of instructions from the analyte monitoring device (e.g., any variety of hand-held analyte measurement instruments or analysis instruments, such as a reader for instance).

In one embodiment, analyte levels are monitored at a faster frequency than the frequency at which the analyte levels are logged or otherwise recorded in memory—e.g., to track the history of the analyte levels. The monitored analyte levels obtained at the faster rate is referred to herein as "fast data", while the data recorded at the slower and variable rate is referred to herein as "slow data" or "variable data". The fast data is used to adjust the variable frequency of the slow data. For example, the slow data may be recorded at different frequencies based on the characteristics of the fast data, such as how steady the fast data is, etc. For instance, in one embodiment, when fast data is steady or relatively slow (e.g., having no rate-of-change or small rate-of-change), the device may record the slow data at a slow frequency (e.g., 10, 20, 30 minutes, etc.), and when the fast data is rapidly changing (e.g., having a faster rate-of-change), then the device may record the slow data at a faster frequency (e.g., 1, 2, 5 minutes, etc.). The value of a steady or low rate of change may vary in different embodiments. In some instances, an example of low rates of changes may include, but are not limited to, 2 mg/dL/min or less, such as 1 mg/dL/min or less. The value of a high rate of change may vary in different embodiments. Example high rates of changes may include, but are not limited to 1 mg/dL/min or greater, such as 2 mg/dL/min or greater. The low rate of change and high rate of change may be defined differently or include additional constraints in other embodiments. For example, the definitions and constraints may vary depending on how many data points are used to determine the rate of change, how long the duration of the rate of change exceeds a threshold, etc.

Various frequencies may be implemented for the slow data and fast data in different embodiments. Further, the frequency at which the slow data is recorded and how it is adjusted based on the fast data may be programmed in different manners or based on different criteria. The rate-of-change levels that are used to trigger changes in the variable data may also be used for other reasons, such as determining analyte trends—e.g., as displayed on the user interface of the reader.

In one embodiment, the monitored analyte levels (or fast data) is equivalent to the sampled analyte levels. In other words, the sampled analyte levels are monitored. In another embodiment, the monitored analyte levels are slower than the sampled analyte levels (e.g., every other sampled analyte level, every third sampled analyte level, etc.).

In one embodiment, the monitored analyte levels are stored in memory temporarily to maintain a rolling log for example. The memory may be sized to hold enough monitored analyte levels to determine how to adjust the variable data.

For example, in one embodiment, an on body unit monitoring sampled analyte levels (e.g., glucose levels) at a specific rate or frequency and keeps a rolling log for a predetermined period of time. An example may include, but is not limited to, sampling analyte levels once every minute and keeping a rolling log of 16 minutes. The slow data may then be used to record or otherwise store sampled analyte levels for a longer duration than the rolling log for the fast data. For example, the rolling log for the fast data may be configured for 16 minutes of data, while the memory for the slow data may be able to store data for an 8-hour period. These values are exemplary and other values may be implemented. The slow data recorded may then be sent to a remote receiving unit, such as an analyte monitoring device (e.g., glucose meter or reader), when the receiving unit is brought into communication range with the on body unit including the in-vivo positioned analyte sensor.

Figure 5:
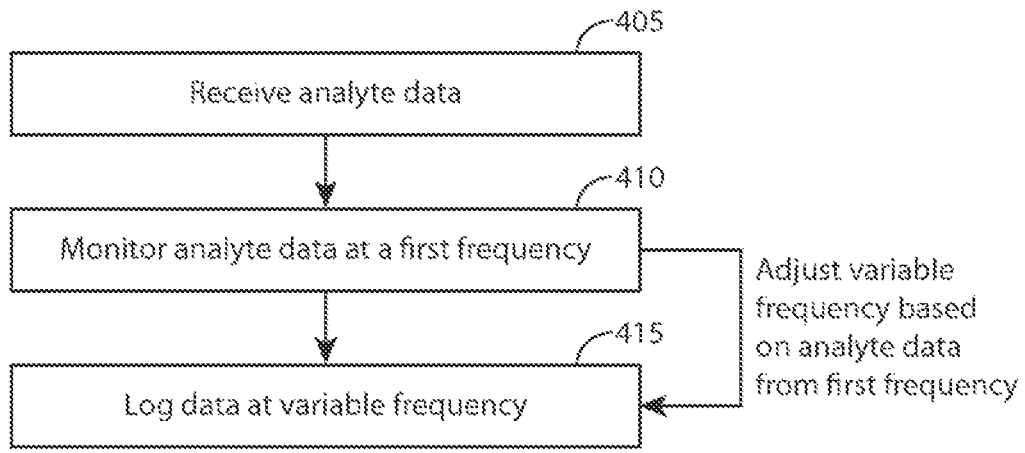
FIG. 5 illustrates a flowchart for logging or otherwise recording data at a variable frequency, according to one embodiment.

FIG. 5 illustrates a flowchart for logging or otherwise recording data at a variable frequency, according to one embodiment. At block 405, analyte levels derived from an in-vivo positioned sensor are received. For example, sensor electronics coupled to the in-vivo positioned analyte sensor may receive the analyte level data as they are sampled. The in-vivo positioned sensor may be sampled every minute. The sampling frequency is exemplary and other sampling frequencies may be implemented.

At block 410, the sampled analyte levels are monitored at a first frequency. In one embodiment, the sampled analyte levels are monitored at the rate at which they are sampled. For example, the analyte levels may be sampled every minute with each sample being monitored. In another embodiment, the sampled analyte levels are monitored at a slower rate than the sampling rate. For example, the analyte levels may be sampled every minute but monitored every other minute. The values provided are exemplary and other values may be implemented.

At block 415, the sampled analyte levels are logged or otherwise recorded at a variable frequency, as represented by block 415. The variable frequency may be set to a slower frequency than the monitored frequency (e.g., every 15 minutes, or some other slower frequency). In one embodiment, the variable frequency may be adjusted to the sampling frequency, which may be the same frequency or faster frequency than the monitored frequency.

The variable frequency is adjusted based on the monitored analyte levels. The analyte levels recorded at the variable frequency (e.g., stored within memory) may then be sent to remote receiving device (e.g., an analyte monitoring device, such as an glucose meter or reader) to provide historical analyte levels for the subject. The logged historical data may be stored over a longer period of time to provide sufficient historical data for analysis.

In one embodiment, the monitoring of the analyte level data at the first frequency includes storing the data in memory—e.g., keeping a rolling log of data for a predetermined period of time. In this way, the data may be accessed and analyzed to determine whether to adjust the variable frequency higher or lower and by how much. In another embodiment, the analyte level data is processed on the fly in real-time and the variable frequency adjusted accordingly.

For example, an on body unit including sensor electronics coupled to an in-vivo positioned glucose sensor can monitor the glucose levels at the sampling rate of a sample per minute, and keep a rolling log of 16 minutes of glucose levels. Every 15 minutes, a glucose level is logged and stored in memory. The 16 minute rolling log of glucose data is analyzed or otherwise processed (e.g., by a processor of the sensor electronics) to determine whether to adjust the variable frequency and by how much. For instance, if the glucose data in the 16 minute rolling log is steady or slow changing (e.g., below a predetermined threshold rate-of-change), then the processor records the variable data at a slower frequency than if the glucose data in the 16 minute rolling log is rapidly changing. The variable data stored in memory may then be subsequently communicated (e.g., wirelessly) to a glucose monitoring device, such as a glucose meter or reader.

In some aspects, analyte levels are monitored at a faster frequency than the frequency at which the analyte levels are logged or otherwise recorded in memory, but the frequency of the variable data is adjusted based upon communications with an analyte monitoring device or other device. The analyte monitoring device or other device may communicate frequency-adjusting information to the sensor electronics of the on body unit that is then used to determine whether to adjust the recording frequency of the variable data. The communication of the information and/or the adjustments of the recording frequency may occur at discrete times or otherwise be performed dynamically in real-time.

In one embodiment, the variable data frequency may be adjusted based one or more of the following: information for certain preset conditions (e.g., time of day, user indicated activity, etc.); input information from a device (e.g., a pedometer or accelerometer (e.g., for exercise or sleep); information relating to an insulin pump, smart pen, bolus calculator (e.g., for meal or insulin delivery), etc.), etc.

Figure 6:
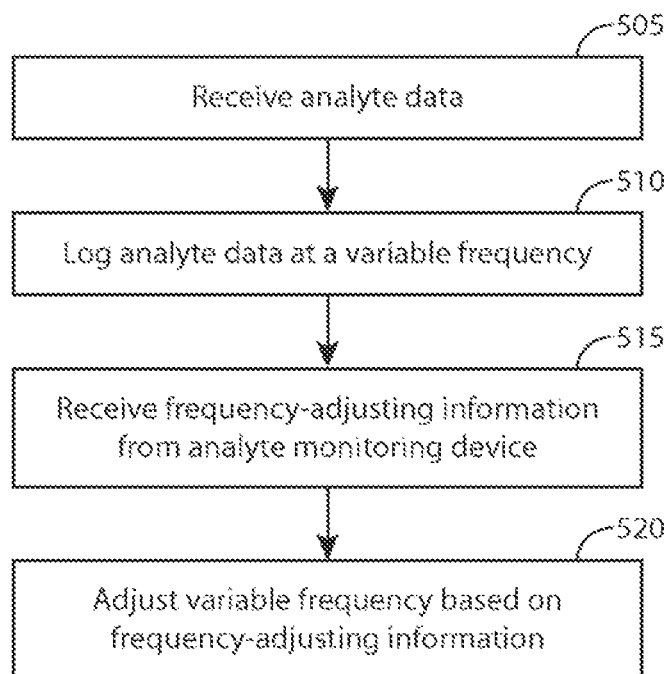
FIG. 6 illustrates a flowchart for logging or otherwise recording data at a variable frequency, according to one embodiment.

FIG. 6 illustrates a flowchart for logging or otherwise recording data at a variable frequency, according to one embodiment. At block 505, analyte levels derived from an in-vivo positioned sensor are received. For example, sensor electronics coupled to an in-vivo positioned analyte sensor of an on body unit may receive the analyte levels derived from the in-vivo positioned analyte sensor as they are sampled. The analyte level data is logged into memory at a variable frequency. At block 515, the sensor electronics receive frequency-adjusting information from an analyte monitoring device or other analyte-related device configured to communicate with the sensor electronics. The devices may be in constant communication range, or brought into communication range at various times for instance. At block 520, the sensor electronics adjusts the frequency at which the variable data is recorded based on the frequency-adjusting information. For instance, the frequency may be increased around meal times, during exercise, before and after insulin administration times. The frequency may be decreased, for instance, during sleeping hours or other times when glucose would be expected to be most stable. The preceding adjustments are exemplary, and the variable frequency may be adjusted according to any predefined parameters or criteria.

Randomly Acquiring or Logging Analyte Levels:

In some aspects, methods, devices, and systems related to analyte monitoring with in-vivo positioned analyte sensors by acquiring or storing analyte levels from the in-vivo positioned analyte sensor at randomly determined periods of time. In this way, for example, diagnosis or evaluation of subjects (e.g., diabetic patients) may not rely solely on point-in-time analyte levels (e.g., fasting glucose analyte levels, etc.) or a single number that reflects the average glucose level over a 3 month period (e.g., A1c analyte levels, etc.).

In one embodiment, an on body unit is activated to begin a random testing process in which analyte levels are randomly sampled or otherwise acquired. The activation of the random testing process by the microprocessor can be done externally, for example, such as by bringing an analyte monitoring device into communication range with the on body unit.

The testing process is random in that there is no preprogrammed schedule of times to perform a testing, or preprogrammed frequency at which testings are performed. The user of the device, whether the doctor, health care provider, or patient, does not select or choose the testing schedule or frequency of the testing times. Instead, the sensor electronics (e.g., processor) of the on body unit randomly determines the testing times at which a testing is performed. The testing may be determined under broad constraints not specific to the times at which the testings are performed, however, such as a predetermined or minimal number of readings, or a predetermined or minimal number of readings in a predetermined time period, etc. For instance, a broad constraint may be that 6 glucose readings are to be performed in a 24-hour period. These values are exemplary and other numbers of readings or time periods may be implemented. The constraints may be based on both clinical factors (e.g., minimal number of readings that are required to make useful clinical decisions) and technical considerations (e.g., memory capacity of storage unit within the sensor). However, the actual timing of the performance of the testing is random.

Following activation, the processor determines the time at which the analyte level (e.g., glucose level) is stored in memory. In one embodiment, the sensor measures the analyte level only at the time when the analyte level is to be stored in memory. For example, using the example of 6 glucose readings in a 24-hour period, the following is an example of random times at which a glucose reading is measured and recorded in memory. The example is not intended to be limiting.

Day 1: 2 am, 7 am, 3 pm, 8 pm, 10 pm, and 11 pm
Day 2: 5 am, 8 am, 10 am, 11 am, 6 pm, 11 pm
Day 3: 1 am, 10 am, 11 am, 3 pm, 5 pm, 9 pm
. . .
Day n: 1 am, 3 am, 5 am, 2 pm, 8 pm, 11 pm In another embodiment, the on body unit is configured to provide measurements of analyte levels at a predetermined schedule, however the analyte level is stored in memory at randomly generated times. For example, the sensor may measure glucose at some predetermined schedule (e.g., 7 AM, 8 AM, 9 AM . . . ); however, the glucose reading at all these times would not be stored. Only glucose data that would be stored would be that measured at some randomly generated times (e.g., 7 AM, 8 AM, 11 AM, 5 PM . . . ).

The on body unit may then, for instance, communicate (e.g., wired or wirelessly) with the analyte monitoring device to send the randomly stored analyte levels to the analyte monitoring device. The analyte monitoring device, such as any variety of hand-held measurement instruments or analysis instruments, such as a reader for instance. The analyte monitoring device may also be another data processing device such as a personal computer, laptop, cell phone or smartphone, personal digital assistant (PDA), etc.

In one embodiment, the subject has the on body unit coupled to their body with the analyte sensor positioned in vivo for a fixed amount of time. Various values of the fixed amount of time may be implemented in various embodiments. For example, in some instances, the fixed amount of time may be a value between two to 30 days, such as five to ten days. Other fixed amounts of time may also be implemented.

Figure 7:
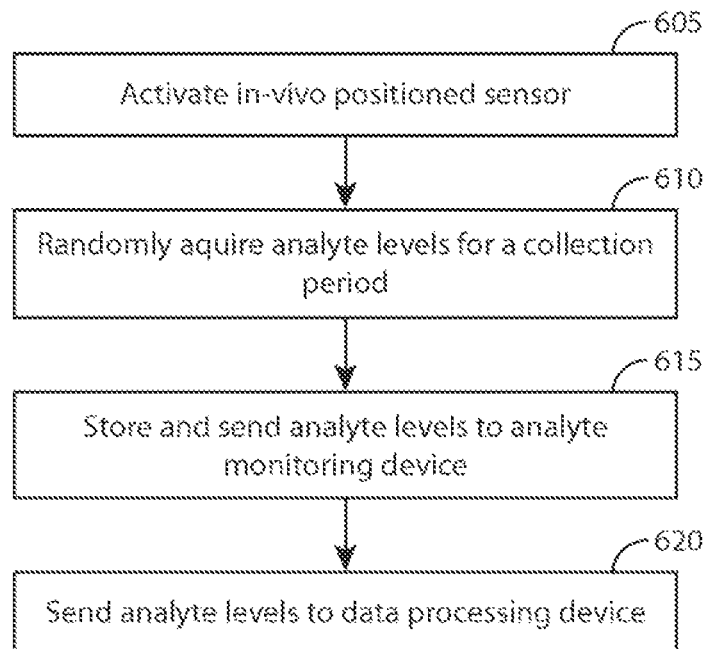
FIG. 7 illustrates a flowchart for randomly acquiring analyte levels from an in-vivo positioned analyte sensor for subsequent analysis, according to one embodiment.

FIG. 7 illustrates a flowchart for randomly acquiring analyte levels from an in-vivo positioned analyte sensor for subsequent analysis, according to one embodiment. At block 605, an on body unit is activated with the analyte sensor positioned in vivo on a subject. At block 610, analyte levels are acquired at random times during a collection period—e.g., from the in-vivo positioned analyte sensor. The randomly acquired analyte data is then stored in memory of the on body unit and subsequently sent to an analyte monitoring device configured to communicate with the on body unit—e.g., when the user initiates a communication between the analyte monitoring device and the on body unit, as represented by block 615. The analyte monitoring device may then send the randomly acquired analyte levels to another data processing device, such as a laptop, computer, smartphone, etc., or to a server via an internet connection, etc., for access by a physician or health care provider for instance, as represented by block 620.

In one embodiment, the randomly acquired analyte levels for the entire collection period is stored and sent to an analyte monitoring device or data processing device during a single communication. In another embodiment, the randomly acquired analyte levels for the entire collection period is sent to an analyte monitoring device or data processing device over multiple communications. For instance, the subject may initiate communications between the on body unit and an analyte monitoring device by bringing the analyte monitoring device in communication range of the on body unit), whereby any randomly acquired analyte levels stored in memory at the time of the communication is sent to the analyte monitoring device.

The physician or health care provider may then obtain the randomly stored analyte data for the entire collection period. For instance, the physician may upload the data from the subject's analyte monitoring device, or from the on body unit, when the subject returns for a follow up visit. Alternatively, the physician may have access to the stored analyte data after the subject uploads the data from the analyte monitoring device to a hospital server via the internet.

Figure 8:
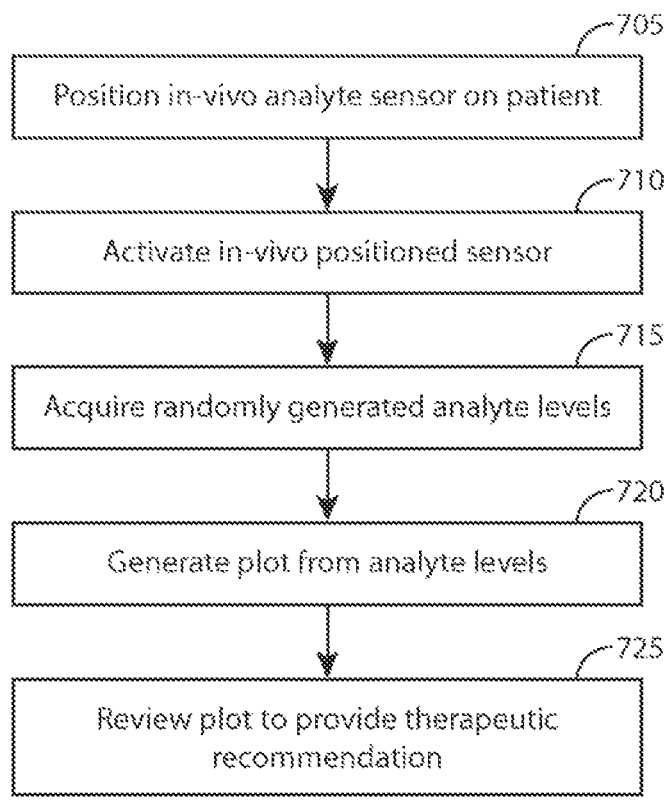
FIG. 8 illustrates a flowchart for a method of providing therapeutic recommendations based on randomly acquired analyte levels derived from an in-vivo positioned analyte sensor.

FIG. 8 illustrates a flowchart for a method of providing therapeutic recommendations based on randomly acquired analyte levels derived from an in-vivo positioned analyte sensor. At block 705, an on body unit is positioned in vivo on a subject. The on body unit is activated, as show at block 710. Analyte levels are randomly acquired and stored in memory in the sensor electronics. At block 715, the randomly acquired analyte levels are retrieved by the physician or health care provider (e.g., from the subject's analyte monitoring device, from the on body unit, or from the hospital server after the subject uploads the data via the internet, etc.). One or more plots are generated from the randomly acquired analyte levels, as represented by block 720. The plots may include, for example, curves of average analyte readings and/or one or more standard deviation lines (e.g., +/−65% range, +/−90% range, etc.) over a predetermined time period, such as a 24-hour period, etc. The physician or health care provider may then review the plot and provide a therapeutic recommendation based on the generated plot, as represented by block 725.

Figure 9:
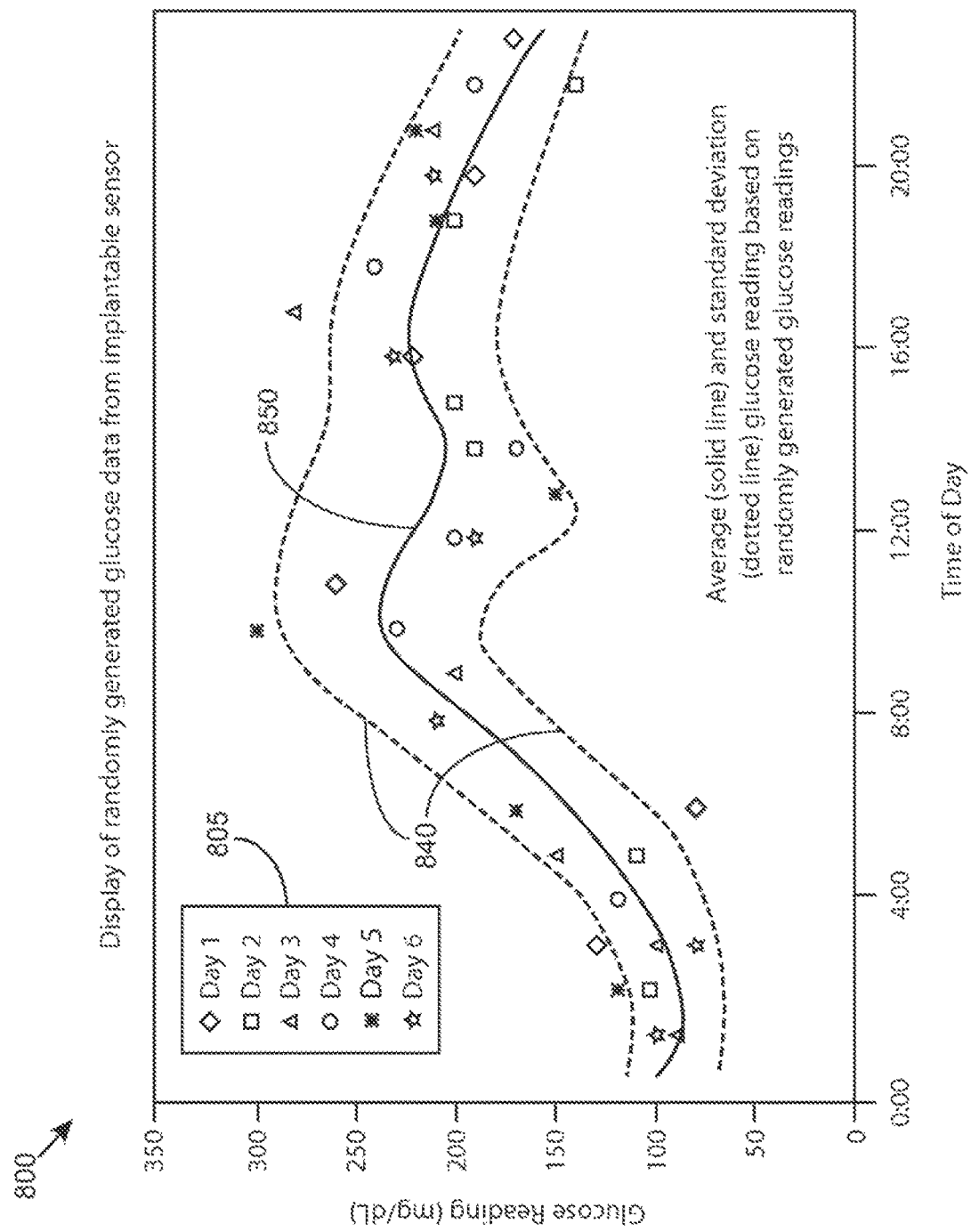
FIG. 9 illustrates a plot of randomly acquired glucose levels derived from an in-vivo positioned glucose sensor, according to one embodiment.

FIG. 9 illustrates a plot of randomly acquired glucose levels derived from an on body unit, according to one embodiment. Plot 800 includes randomly acquired glucose levels 805 derived from an in-vivo positioned glucose sensor over six days. An average glucose curve 850 generated from the randomly acquired analyte levels 805 is shown on the plot. Also shown are the standard deviation curves 840 generated from the randomly acquired analyte levels 805.
Configuring Recording Parameters:

Various analyte monitoring devices and systems may require different design parameters, such as memory size needed (e.g., to save sufficient data, save space, or to save on cost), and/or the appropriate sampling or recording rate or interval, etc.

In some embodiments, the analyte levels are sent to an analyte monitoring device, which remains in communication range with the on body unit. In other embodiments, the analyte levels are sent to an analyte monitoring device, which is brought in and out of communication range with the on body unit. Further, analyte monitoring devices and systems may be used to provide various analyte related data. For example, glucose systems may in some instances provide the user with real-time glucose information to make an insulin dosing decision; "trends" or rate-of-change information—e.g., an instantaneous value of the rate-of-change represented as a change in glucose concentration per delta time; or "trend" information that represents characteristics of glucose values with respect to the rate-of-change, such as increasing (e.g., rising), increasing rapidly, decreasing (e.g., falling), decreasing rapidly, remaining level (e.g., stable), etc. Still further, analyte monitoring systems may also store past analyte values and present one or more of the past values to the user. In some instance a single past value (e.g., the most recent past value) may be presented. In other instances, multiple glucose values may be presented over a time period—e.g., over the last hour, 8 hours, 12 hours, 24 hours, etc.

The specific implementation and application of the device or system may require different design parameters (e.g., memory sizes, sampling rates, etc.) for optimum monitoring. For instance, the amount of memory needed for historic data may depend on various factors, such as how the system is used, etc. For example, a system intended for viewing historical data retrospectively may be include sufficient memory to store the historical data obtained between transfers of the data to the reader. Furthermore, memory size may be affected by cost and space of a device. Having too much memory burdens every unit with the cost of extra memory and further may take up more physical space on the circuit board. Having too little memory may be detrimental to providing enough information to the user to be useful.

The rate at which data points are stored (e.g., every minute, every five minutes, every 10 minutes, etc.) may vary depending on application. In some embodiments, the all sampled data is stored, such that the recording interval or frequency is equal to the sampling interval frequency. In some cases, analyte system may be used by an insulin dependent user to make insulin dosing decisions. In such case, the system needs sufficient memory to retain history for the longer of user's insulin action time (e.g., the time for the insulin taken by the user to effectively run its course in the body of the user) and/or carbohydrate action time (e.g., the time for carbohydrates to effectively run its course in the body of the user). These times may be affected by any number of factors, such as a user's physiological characteristics, type of insulin (e.g., short-acting or long-acting insulin), etc. In some instances, for example, these times may be on the order of a few hours.

Furthermore, the historical recording time or duration, and the number of minutes between saved data points (e.g., the recording rate) may vary depending on the specifics of the application, and/or an individual user's physiological time constant, etc. For instance, the design parameters may be selected by a system designer to save data often enough that significant analyte data points are not missed.

In some aspects of the present disclosure, methods, devices, and systems are provided that enable the configuration of the recording parameters as the system is being used or otherwise operated. The recording parameters may include, for example, the recording duration (e.g., the duration of time that data points should be sampled and stored), the recording rate (e.g., the intervals between samples), etc.

For example, a system designer and/or a user (e.g., a physician, health care provider, patient, etc.) may configure the recording parameters as the system is being used or otherwise operated. In this way, for example, the on body unit may be designed with a modest amount of memory and the system designer and/or user may make the best use of the available memory already implemented in the device. This may provide the benefit, for example, of postponing the decision of how to allocate log memory to fit diverse needs at least until manufacturing time. In this way, the software development process is benefited as the time interval can be changed without a code change and quality assurance cycle. For example, if two or more distinct uses for the on body unit (e.g., masked or unmasked use), then the settings may be adjusted as the system is activated by the user, saving the cost of documenting and stocking different parts for instance.

In one embodiment, for example, the system designer or user may initiate one or more commands to provide the on body unit with user configuration data. For example, the historical data period may be passed from the analyte monitoring device to the on body unit in the commands. The system may then calculate a sampling rate using the user configuration data as well as specification data for the on body unit (e.g., the available memory for storing analyte values). For example, if the on body unit has memory for 24 data points, and user configuration data indicates that a user's insulin action time is 4 hours, the on body unit may be configured to save a historical data point every 10 minutes (e.g., 4 hours*60 minutes per hour/24 samples=10 minutes per sample). As another example, a user reads a glucose value at least once every 12 hours and does not want to miss any data for retrospective analysis. In such case, for example, if the memory capacity is 24 data points, then the on body unit may be configured to save historical data every 30 minutes (e.g., 12 hours*60 minutes per hour/24 samples=30 minutes per sample.

Figure 10:
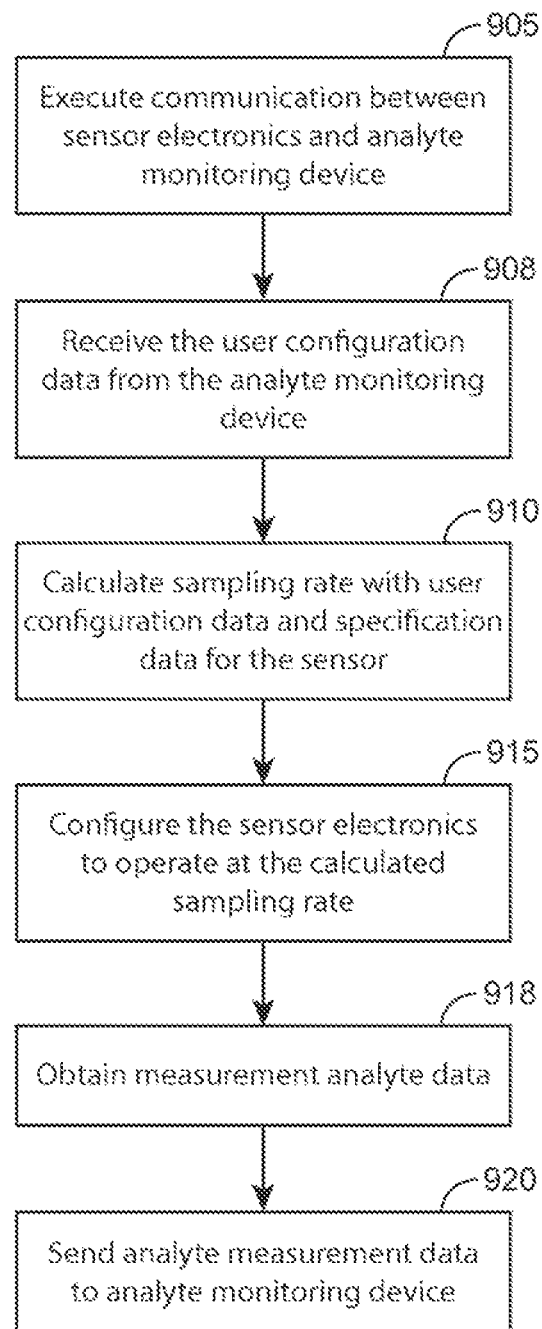
FIG. 10 illustrates a flowchart for configuring sensor electronics to operate at a calculated sampling rate, according to certain embodiments.

FIG. 10 illustrates a flowchart for configuring sensor electronics of the on body unit to operate at a calculated sampling rate, according to certain embodiments. After the sensor electronics execute a communication with the analyte monitoring device (e.g., analyte reader) at block 905, the sensor electronics receives the user configuration data from the analyte monitoring device, as represented by block 908. The sensor electronics calculate the sampling rate with the user configuration data and specification data that is stored in memory of the sensor electronics for instance, as shown by block 910, and then the sensor electronics are configured to sample the in-vivo positioned analyte sensor at the calculated sampling rate, as shown by block 915. The sensor electronics obtains analyte levels at the sampling rate, as shown at block 918, and eventually sends the analyte measurements to an analyte monitoring device or other data processing device, as shown at block 920.

Devices and Systems

In some aspects, the present disclosure relates to the detecting of at least one analyte, including glucose, in body fluid. For example, embodiments may relate to in vivo monitoring of the level of one or more analytes using analyte monitoring device or system and/or the communication of the data derived therefrom. For instance, the system may include an analyte sensor at least a portion of which is to be positioned beneath a skin surface of a user for a period of time.

Embodiments may include combined or combinable devices, systems and methods and/or transferring data within or between an on body unit and an analyte monitoring device. In one embodiment, the systems, or at least a portion of the systems, are integrated into a single unit. In some aspects, the devices, systems, and methods may relate to data processing devices (e.g., a computer, laptop, mobile phone, personal computer, or any other data processing device) that receive or otherwise obtain data derived from the described analyte monitoring systems and devices.

The analyte monitoring devices and systems may include, or communicate with, an on body unit including an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a communication module or the like), a receiver/display unit, transceiver, processor, etc. The sensor may be, for example, positionable in vivo in a user for the monitoring of a level of an analyte in the user's interstitial fluid.

An analyte sensor may be positioned in contact with interstitial fluid to detect the level of glucose, which detected glucose may be used to infer the glucose level in the user's bloodstream. Embodiments of the analyte sensors may be configured for monitoring the level of the analyte over a time period which may range from seconds, minutes, hours, days, weeks, to months, or longer. In some instances, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more.

Embodiments of the present disclosure may relate to the transferring or communication (e.g., logging, storing, communicating, etc.) of the data derived from an analyte monitoring device or system.

As demonstrated herein, the methods of the present disclosure are useful in connection with a device or system that is used to measure or monitor an analyte (e.g., glucose), and/or communicate or process data derived from the measurement or monitoring of an analyte, such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof.

Figure 11:
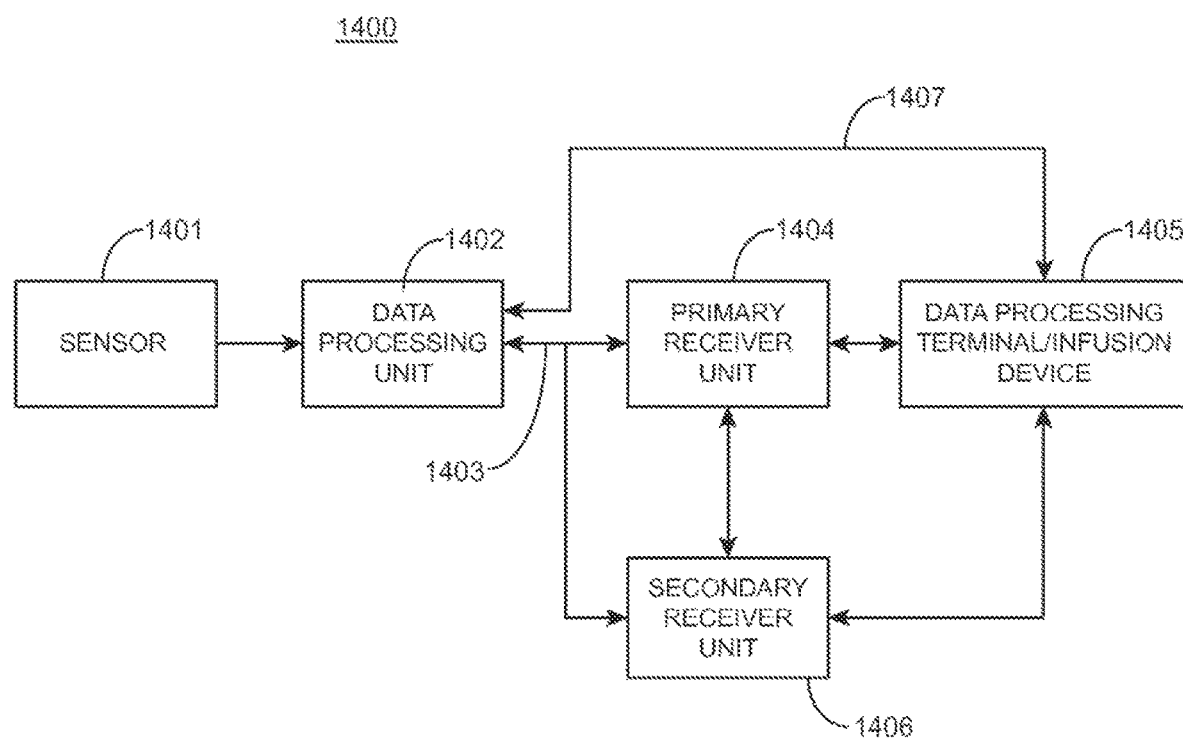
FIG. 11 shows an analyte monitoring system, according to one embodiment.

FIG. 11 shows an analyte (e.g., glucose) monitoring system, according to one embodiment. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 1400 includes an analyte sensor 1401, a data processing unit 1402 connectable to the sensor 1401, and a primary receiver unit 1404. In some instances, the primary receiver unit 1404 is configured to communicate with the data processing unit 1402 via a communication link 1403. In one embodiment, the primary receiver unit 1404 may be further configured to communicate data to a data processing terminal 1405 to evaluate or otherwise process or format data received by the primary receiver unit 1404. The data processing terminal 1405 may be configured to receive data directly from the data processing unit 1402 via a communication link 1407, which may optionally be configured for bi-directional communication. Further, the data processing unit 1402 may include a communication unit or a transceiver to communicate and/or receive data to and/or from the primary receiver unit 1404 and/or the data processing terminal 1405 and/or optionally a secondary receiver unit 1406.

Also shown in FIG. 11 is an optional secondary receiver unit 1406 which is operatively coupled to the communication link 1403 and configured to receive data communicated from the data processing unit 1402. The secondary receiver unit 1406 may be configured to communicate with the primary receiver unit 1404, as well as the data processing terminal 1405. In one embodiment, the secondary receiver unit 1406 may be configured for bi-directional wireless communication with each of the primary receiver unit 1404 and the data processing terminal 1405. As discussed in further detail below, in some instances, the secondary receiver unit 1406 may be a de-featured receiver as compared to the primary receiver unit 1404, for instance, the secondary receiver unit 1406 may include a limited or minimal number of functions and features as compared with the primary receiver unit 1404. As such, the secondary receiver unit 1406 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 1404. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 1401, data processing unit 1402 and data processing terminal 1405 are shown in the embodiment of the analyte monitoring system 1400 illustrated in FIG. 11. However, the analyte monitoring system 1400 may include more than one sensor 1401 and/or more than one data processing unit 1402, and/or more than one data processing terminal 1405. Multiple sensors may be positioned in a user for analyte monitoring at the same or different times.

The analyte monitoring system 1400 may be a continuous monitoring system, or semi-continuous, or a monitoring system that provides for transfer of analyte levels only upon brining of the on body unit and analyte monitoring device in signal communication with one another (flash). In a multi-component environment, each component may be configured to be uniquely identified by one or more of the other components in the system so that communication conflict may be readily resolved between the various components within the analyte monitoring system 1400. For example, unique IDs, communication channels, and the like, may be used.

In one embodiment, the sensor 1401 is physically positioned in or on the body of a user whose analyte level is being monitored. The sensor 1401 may be configured to at least periodically sample the analyte level of the user and convert the sampled analyte level into a corresponding signal for communication by the data processing unit 1402. The data processing unit 1402 is coupleable to the sensor 1401 so that both devices are positioned in or on the user's body, with at least a portion of the analyte sensor 1401 positioned transcutaneously. The data processing unit may include a fixation element, such as an adhesive or the like, to secure it to the user's body. A mount (not shown) attachable to the user and mateable with the data processing unit 1402 may be used. For example, a mount may include an adhesive surface. The data processing unit 1402 performs data processing functions, where such functions may include, but are not limited to, filtering and encoding of data signals, each of which corresponds to a sampled analyte level of the user, for communication to the primary receiver unit 1404 via the communication link 1403. In one embodiment, the sensor 1401 or the data processing unit 1402 or a combined sensor/data processing unit may be wholly implantable under the skin surface of the user.

In one embodiment, the primary receiver unit 1404 may include an analog interface section including an RF receiver and an antenna that is configured to communicate with the data processing unit 1402 via the communication link 1403, and a data processing section for processing the received data from the data processing unit 1402 including data decoding, error detection and correction, data clock generation, data bit recovery, etc., or any combination thereof.

In operation, the primary receiver unit 1404 in one embodiment is configured to synchronize with the data processing unit 1402 to uniquely identify the data processing unit 1402, based on, for example, an identification information of the data processing unit 1402, and thereafter, to periodically receive signals communicated from the data processing unit 1402 associated with the monitored analyte levels detected by the sensor 1401.

Referring again to FIG. 11, the data processing terminal 1405 may include a personal computer, a portable computer including a laptop or a handheld device such as a consumer electronics device (e.g., a personal digital assistant (PDA), a telephone including a cellular phone (e.g., a multimedia and Internet-enabled mobile phone including an iPhone™, a Blackberry °, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 1405 may further be connected to a data network (not shown) for storing, retrieving, updating, and/or analyzing data corresponding to the detected analyte level of the user.

The data processing terminal 1405 may include a drug delivery device (e.g., an infusion device) such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 1404 may be configured to integrate an infusion device therein so that the primary receiver unit 1404 is configured to administer an appropriate drug (e.g., insulin) to users, for example, for administering and modifying basal profiles, as well as for determining appropriate boluses for administration based on, among others, the detected analyte levels received from the data processing unit 1402. An infusion device may be an external device or an internal device, such as a device wholly implantable in a user.

In one embodiment, the data processing terminal 1405, which may include an infusion device, e.g., an insulin pump, may be configured to receive the analyte signals from the data processing unit 1402, and thus, incorporate the functions of the primary receiver unit 1404 including data processing for managing the user's insulin therapy and analyte monitoring. In one embodiment, the communication link 1403, as well as one or more of the other communication interfaces shown in FIG. 11, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 12:
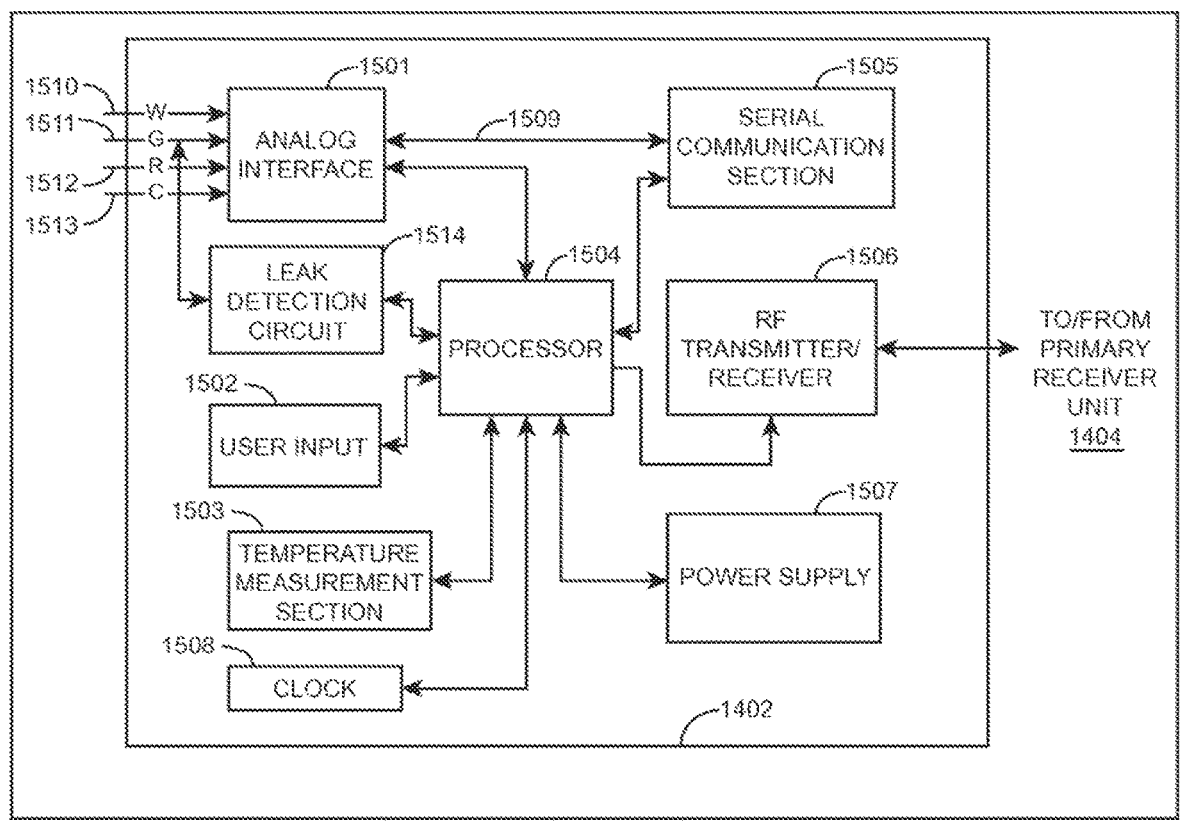
FIG. 12 is a block diagram of the data processing unit shown in FIG. 11, according to one embodiment.

FIG. 12 is a block diagram of the data processing unit 1402 shown in FIG. 11 in accordance with one embodiment. Data processing unit 1402 includes an analog interface 1501 configured to communicate with the sensor 1401 (FIG. 1), a user input 1502, and a temperature measurement section 1503, each of which is operatively coupled to processor 1504 such as a central processing unit (CPU). Furthermore, unit 1402 is shown to include a serial communication section 1505, clock 1508, and a communication unit 1506, each of which is also operatively coupled to the processor 1504. Moreover, a power supply 1507 such as a battery is also provided in unit 1402 to provide the necessary power.

In another embodiment, the data processing unit may not include all components in the exemplary embodiment shown. User input and/or interface components may be included or a data processing unit may be free of user input and/or interface components. In one embodiment, one or more application-specific integrated circuits (ASIC) may be used to implement one or more functions or routines associated with the operations of the data processing unit (and/or receiver unit) using for example one or more state machines and buffers.

As can be seen in the embodiment of FIG. 12, the analyte sensor 1401 (FIG. 1) includes four contacts, three of which are electrodes: a work electrode (W) 1510, a reference electrode (R) 1512, and a counter electrode (C) 1513, each operatively coupled to the analog interface 1501 of the data processing unit 1402. This embodiment also shows an optional guard contact (G) 1511. Fewer or greater electrodes may be employed. For example, the counter and reference electrode functions may be served by a single counter/reference electrode. In some cases, there may be more than one working electrode and/or reference electrode and/or counter electrode, etc.

Figure 13:
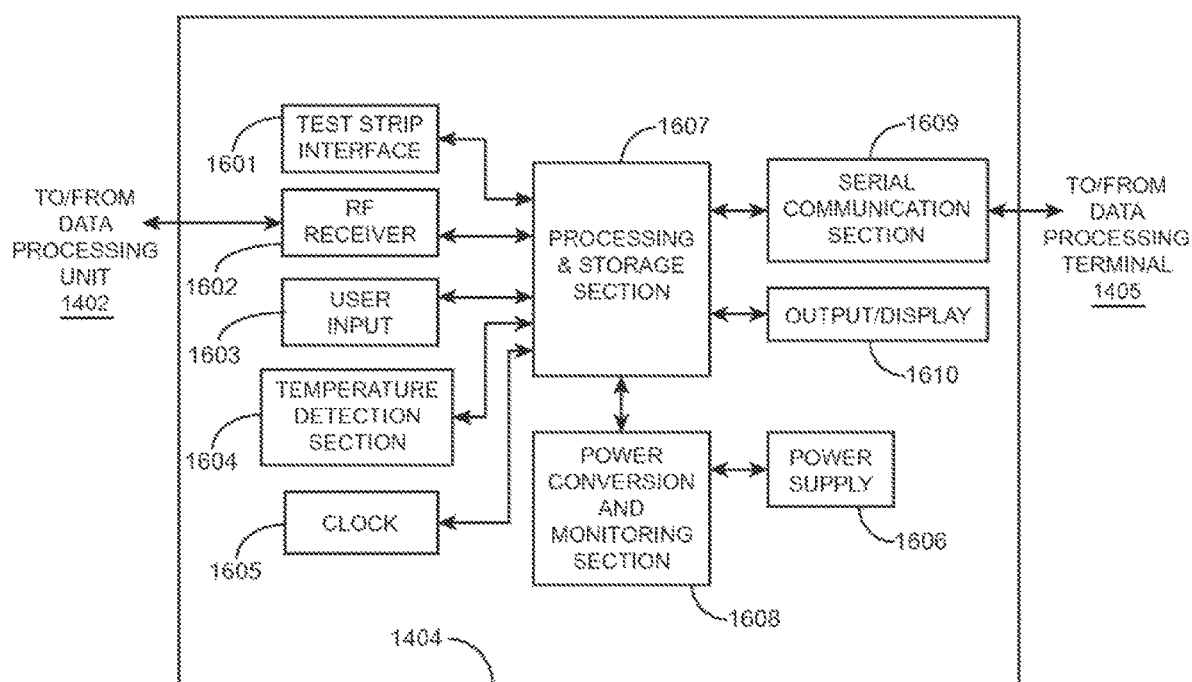
FIG. 13 is a block diagram of an embodiment of a receiver/monitor unit such as the primary receiver unit of the analyte monitoring system shown in FIG. 11, according to one embodiment.

FIG. 13 is a block diagram of an embodiment of a receiver/monitor unit such as the primary receiver unit 1404 of the analyte monitoring system shown in FIG. 11. The primary receiver unit 1404 includes one or more of: a test strip interface 1601, an RF receiver 1602, a user input 1603, an optional temperature detection section 1604, and a clock 1605, each of which is operatively coupled to a processing and storage section 1607. The primary receiver unit 1404 also includes a power supply 1606 operatively coupled to a power conversion and monitoring section 1608. Further, the power conversion and monitoring section 1608 is also coupled to the processing and storage section 1607. Moreover, also shown are a receiver serial communication section 1609, and an output 1610, each operatively coupled to the processing and storage section 1607. The primary receiver unit 1404 may include user input and/or interface components or may be free of user input and/or interface components.

In one embodiment, the test strip interface 1601 includes an analyte testing portion (e.g., a glucose level testing portion) to receive a blood (or other body fluid sample) analyte test or information related thereto. For example, the test strip interface 1601 may include a test strip port to receive a test strip (e.g., a glucose test strip). The device may determine the analyte level of the test strip, and optionally display (or otherwise notice) the analyte level on the output 1610 of the primary receiver unit 1404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., Freestyle® and Precision® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 1401, confirm results of sensor 1401 to increase the confidence thereof (e.g., in instances in which information obtained by sensor 1401 is employed in therapy related decisions), etc.

In further embodiments, the data processing unit 1402 and/or the primary receiver unit 1404 and/or the secondary receiver unit 1406, and/or the data processing terminal/infusion device 1405 may be configured to receive the analyte value wirelessly over a communication link from, for example, a blood glucose meter. In further embodiments, a user manipulating or using the analyte monitoring system 1400 (FIG. 11) may manually input the analyte value using, for example, a user interface (for example, a keyboard, keypad, voice commands, and the like) incorporated in one or more of the data processing unit 1402, the primary receiver unit 1404, secondary receiver unit 1406, or the data processing terminal/infusion device 1405.

The features and techniques described in the present disclosure may be performed, for example, by the processing circuitry within the data processing unit 1402 or receiving unit 1404, or combination of both. For example, in certain embodiments, one or more of the above-described methods may be performed entirely within the sensor electronics coupled to the in vivo positioned analyte sensor. In yet other embodiments, one or more of the above-described methods may be performed entirely within the receiver unit or electronics that receive the analyte levels from the sensor electronics. In yet other embodiments, one or more of the above-described methods may be performed by a combination of the sensor electronics and receiver electronics. In yet other embodiments, one or more of the above-describe methods may be performed entirely, or in part, by a data processing device that is provided with the analyte levels derived from the in vivo positioned analyte sensor.

Additional detailed descriptions are provided in U.S. Pat. Nos. 5,262,035; 5,264,104; 5,262,305; 5,320,715; 5,593,852; 6,175,752; 6,650,471; 6,746, 582, and 7,811,231, each of which is incorporated herein by reference in their entirety.

In one embodiment of the present disclosure, the analyte monitoring device includes processing circuitry that is able to determine a level of the analyte and activate an alarm system if the analyte level exceeds a threshold. The analyte monitoring device, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range may be 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. patent applications, and/or non-U.S. patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially in vivo positioned sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

Additional Example Embodiments

In some aspects, methods of recording sampled analyte levels with an on body unit are provided that include obtaining analyte levels derived from an in vivo sensor sampled at sampling intervals; and recording, with a processor, sampled analyte levels in memory at recording intervals. The recording intervals include more than one sampling interval. The recorded analyte levels are subject to a validity determination before being recorded. One or more of the validity determinations are performed on a sampled analyte level coinciding with a time point of a recording interval, and one or more of the validity determinations are performed on a sampled analyte level not coinciding with a time point of a recording interval.

In certain embodiments, the methods include selecting a first sampled analyte level coinciding with a first time point of the recording intervals; performing a first validity determination on the first coinciding analyte level; determining the first coinciding analyte level is valid; and recording the first coinciding analyte level determined is valid.

In certain embodiments, the methods include selecting a second sampled analyte level coinciding with a second time point of the recording intervals; performing a second validity determination on the second coinciding analyte level; determining the second coinciding analyte level is invalid; selecting a first alternative analyte level for validity determination; and performing a third validity determination on the first alternative analyte level. Further, the first alternative analyte level is a sampled analyte level that does not coincide with a time point of the recording intervals.

In certain embodiments, the methods include determining the first alternative analyte level is valid; and recording the first alternative analyte level instead of the second coinciding analyte level.

In certain embodiments, the methods include determining the first alternative analyte level is invalid; and selecting a second alternative analyte level for validity determination; performing a fourth validity determination on the second alternative analyte level; determining the second alternative analyte level is valid; and recording the second alternative analyte level instead of the second coinciding analyte level. Further, the second alternative analyte level is a sampled analyte level that does not coincide with a time point of the recording intervals.

In certain embodiments, the methods include determining the first alternative analyte level is invalid; and selecting one or more alternative analyte levels for validity determinations; performing a validity determination on each of the one or more alternative analyte levels until a valid determination is made; and recording an alternative analyte level generating the valid determination instead of the second coinciding analyte level. Further, the one or more alternative analyte levels are sampled analyte levels that do not coincide with a time point of the recording intervals.

In certain embodiments, the first alternative analyte level is a sampled analyte level immediately adjacent to the second coinciding analyte level.

In certain embodiments, each alternative analyte level is distanced within a recording window for the second time point, wherein the recording window is defined by recording time points immediately prior to and immediately subsequent to the second time point.

In certain embodiments, an adjusted timestamp is recorded with the recorded alternative analyte level.

In certain embodiments, the methods include selecting a first sampled analyte level coinciding with a first time point of the recording intervals; selecting one or more alternative analyte level for validity determination; generating a validity metric for the first coinciding analyte level and the one or more alternative analyte levels; and recording an analyte level based on the validity metrics for the first coinciding analyte level and the one or more alternative analyte levels. Further, the one or more alternative analyte levels are sampled analyte levels that do not coincide with a time point of the recording intervals. Still further, the validity metrics for the coinciding analyte level and the one or more alternative analyte levels represent a level of validity.

In certain embodiments, the validity metrics are weighed based on a time deviation from the first time point, and wherein the recording of the analyte level is based on the weighted validity metrics.

In certain embodiments, each of the one or more alternative analyte levels are distanced within a recording window for the first time point, wherein the recording window is defined by recording time points immediately prior to and immediately subsequent to the first time point.

In certain embodiments, missing analyte levels are determined to be invalid.

In certain embodiments, sampled analyte levels are stored in a buffer.

In certain embodiments, the analyte is glucose or a ketone body.

In some aspects, analyte monitoring devices are provided that include an in-vivo positionable analyte sensor; and sensor electronics coupled to the in-vivo positionable sensor. The sensor electronics includes a processor and memory operably coupled to the processor. The memory includes instructions stored therein that, when executed by a processor, cause the processor to obtain analyte levels derived from an in vivo sensor sampled at sampling intervals; and record, with a processor, sampled analyte levels in memory at recording intervals, the recording intervals including more than one sampling interval. The recorded analyte levels are subject to a validity determination before being recorded. The one or more of the validity determinations are performed on a sampled analyte level coinciding with a time point of a recording interval. One or more of the validity determinations are performed on a sampled analyte level not coinciding with a time point of a recording interval.

In certain embodiments, the memory includes instructions stored therein that, when executed by a processor, cause the processor to select a first sampled analyte level coinciding with a first time point of the recording intervals; perform a first validity determination on the first coinciding analyte level; determine the first coinciding analyte level is valid; and record the first coinciding analyte level determined is valid.

In certain embodiments, the memory includes instructions stored therein that, when executed by a processor, cause the processor to select a second sampled analyte level coinciding with a second time point of the recording intervals; perform a second validity determination on the second coinciding analyte level; determine the second coinciding analyte level is invalid; select a first alternative analyte level for validity determination, wherein the first alternative analyte level is a sampled analyte level that does not coincide with a time point of the recording intervals; and perform a third validity determination on the first alternative analyte level.

In certain embodiments, the memory includes instructions stored therein that, when executed by a processor, cause the processor to determine the first alternative analyte level is valid; and record the first alternative analyte level instead of the second coinciding analyte level.

In certain embodiments, the memory includes instructions stored therein that, when executed by a processor, cause the processor to determine the first alternative analyte level is invalid; and select a second alternative analyte level for validity determination; performing a fourth validity determination on the second alternative analyte level; determining the second alternative analyte level is valid; and recording the second alternative analyte level instead of the second coinciding analyte level. The second alternative analyte level is a sampled analyte level that does not coincide with a time point of the recording intervals.

In certain embodiments, the memory includes instructions stored therein that, when executed by a processor, cause the processor to determine the first alternative analyte level is invalid; select one or more alternative analyte levels for validity determinations; perform a validity determination on each of the one or more alternative analyte levels until a valid determination is made; and record an alternative analyte level generating the valid determination instead of the second coinciding analyte level. Further, the one or more alternative analyte levels are sampled analyte levels that do not coincide with a time point of the recording intervals.

In certain embodiments, the first alternative analyte level is a sampled analyte level immediately adjacent to the second coinciding analyte level.

In certain embodiments, each alternative analyte level is distanced within a recording window for the second time point, wherein the recording window is defined by recording time points immediately prior to and immediately subsequent to the second time point.

In certain embodiments, an adjusted timestamp is recorded with the recorded alternative analyte level.

In certain embodiments, the memory includes instructions stored therein that, when executed by a processor, cause the processor to select a first sampled analyte level coinciding with a first time point of the recording intervals; select one or more alternative analyte level for validity determination; generate a validity metric for the first coinciding analyte level and the one or more alternative analyte levels; record an analyte level based on the validity metrics for the first coinciding analyte level and the one or more alternative analyte levels. Further, the one or more alternative analyte level s are sampled analyte levels that do not coincide with a time point of the recording intervals. Further, the validity metrics for the coinciding analyte level and the one or more alternative analyte levels represent a level of validity.

In certain embodiments, the validity metrics are weighed based on a time deviation from the first time point, and wherein the recording of the analyte level is based on the weighted validity metrics.

In certain embodiments, each of the one or more alternative analyte levels are distanced within a recording window for the first time point, wherein the recording window is defined by recording time points immediately prior to and immediately subsequent to the first time point.

In certain embodiments, missing analyte levels are determined to be invalid.

In certain embodiments, sampled analyte levels are stored in a buffer.

In certain embodiments, the analyte is glucose or a ketone body.

In some aspects, methods of configuring a recording rate are provided that include executing a communication between sensor electronics and an analyte monitoring device; receiving user configuration data at the sensor electronics from the analyte monitoring device; calculating a recording rate for the sensor electronics and in-vivo positioned analyte sensor; and configuring the sensor electronics to operate at the calculated recording rate. The sensor electronics are coupled to an in-vivo positionable sensor and configured to communicate analyte levels to the analyte monitoring device. The recording rate is calculated based on user configuration data for the analyte monitoring device; and specification data for the sensor electronics.

In certain embodiments, the methods include obtaining and storing analyte levels form the in-vivo positioned analyte sensor at the recording rate; and sending the analyte levels to the analyte monitoring device.

In certain embodiments, the user configuration data comprises a recording duration.

In certain embodiments, the recording duration is based on an insulin action time and/or a carbohydrate action time.

In certain embodiments, the recording duration is based on a user's reading pattern.

In certain embodiments, the specification data includes sample storage capacity.

In some aspects, analyte monitoring devices are provided that include an in-vivo positionable analyte sensor; and sensor electronics coupled to the in-vivo positionable sensor. The sensor electronics include a processor; and memory operably coupled to the processor. The memory includes instructions stored therein that, when executed by a processor, cause the processor to execute a communication between sensor electronics and an analyte monitoring device; receive user configuration data at the sensor electronics from the analyte monitoring device; calculate a recording rate for the sensor electronics and in-vivo positioned analyte sensor; and configuring the sensor electronics to operate at the calculated recording rate. The sensor electronics are coupled to an in-vivo positionable sensor and configured to communicate analyte levels to the analyte monitoring device. The recording rate is calculated based on: user configuration data for the analyte monitoring device; and specification data for the sensor electronics.

In certain embodiments, the memory includes instructions stored therein that, when executed by a processor, cause the processor to obtaining and recording analyte levels form the in-vivo positioned analyte sensor at the recording rate; and sending the analyte levels to the analyte monitoring device.

In certain embodiments, the user configuration data comprises a recording duration.

In certain embodiments, the recording duration is based on an insulin action time and/or a carbohydrate action time.

In certain embodiments, the recording duration is based on a user's reading pattern.

In certain embodiments, the specification data includes sample storage capacity.

In some aspects, analyte monitoring devices are provided that include a communication interface for receiving analyte levels derived from an on body unit including an in-vivo positioned analyte sensor; a display for displaying analyte value; a processor; and memory operably coupled to the processor. The memory includes instructions stored therein that, when executed by a processor, cause the processor to receive first sensor-use information via the communication interface, wherein the first sensor-use information indicates a first type of sensor-use for a first on body unit; identify first settings associated with the first sensor-use information, wherein the first settings comprise a setting to operate in a mode where analyte values are not displayed on the display; configure the analyte monitoring device to operate with the first settings; and operate the analyte monitoring device with the first settings. Analyte values are not displayed when analyte values are received via the communication interface.

In certain embodiments, the first type of sensor-use is for clinical use, and wherein the second type of sensor-use is for personal use.

In certain embodiments, the first sensor-use information is received during a communication for initially pairing the analyte monitoring device and the sensing device.

In certain embodiments, the sensor-sensor-use information is received during a communication for transferring analyte values from the on body unit to the analyte monitoring device.

In certain embodiments, the memory includes instructions stored therein that, when executed by a processor, cause the processor to receive second sensor-use information via the communication interface, wherein the second sensor-use information indicates a second type of sensor-use for a second on body unit; identify second settings associated with the second sensor-use information, wherein the second settings comprise setting to operate in a mode where analyte values are displayed on the display; configure the analyte monitoring device to operate with the second settings; and operate the analyte monitoring device with the second settings, wherein analyte values are displayed when analyte values are received via the communication interface.

In some aspects, methods for providing therapeutic recommendations based on randomly acquired analyte levels derived from the in-vivo positioned sensor are provided. The methods include positioning an analyte sensor in vivo on a subject, the in vivo positioned analyte sensor coupled to sensor electronics, the sensor electronics include a processor and memory; activating the sensor electronics for operation with the in-vivo positioned analyte sensor; randomly acquiring analyte levels derived from the in-vivo positioned sensor over a predetermined period of time for collecting data, wherein the analyte levels are stored in the memory of the sensor electronics; generating a plot from the stored analyte levels; and reviewing the plot to provide therapeutic recommendations.

In certain embodiments, the subject transfers data from the sensor electronics to an analyte monitoring device, and wherein the analyte levels are retrieved from the analyte monitoring device to generate the plot.

In some aspects, analyte monitoring devices are provided that include an in-vivo positionable sensor; sensor electronics coupled to the in-vivo positionable sensor. The sensor electronics include a processor and memory, wherein the memory includes instructions stored therein, which when executed by the processor, cause the processor to randomly acquire analyte levels derived from the in-vivo positionable sensor when positioned in-vivo; and send the randomly acquired analyte levels to a remote device.

In certain embodiments, the remote device is an analyte monitoring device configured to communicate with the sensor electronics.

In certain embodiments, the randomly acquired analyte levels are sampled at a non-random frequency but stored in memory at randomly generated times.

In some aspects, analyte monitoring systems are provided that include an on body unit, comprising: an in-vivo positionable sensor; sensor electronics coupled to the in-vivo positionable sensor; and an analyte monitoring device configured to communicate with the on body unit and receive the randomly acquired analyte levels. The sensor electronics include a processor and memory. The memory includes instructions stored therein, which when executed by the processor, cause the processor to randomly acquire analyte levels derived from the in-vivo positionable sensor when positioned in-vivo; and send the randomly acquired analyte levels to a remote device.

In certain embodiments, the randomly acquired analyte levels are sampled at a non-random frequency but stored in memory at randomly generated times.

In some aspects, methods for storing analyte levels at a variable frequency are provided that include receiving sampled analyte levels derived from an in-vivo positioned sensor; monitoring the sampled analyte levels at a first frequency; and storing the sampled analyte levels at a second frequency, the second frequency slower than the first frequency. The second frequency is variable and determined based on the monitored analyte levels at the first frequency.

In certain embodiments, the second frequency is determined based on a rate of change of the monitored analyte levels at the first frequency, wherein the second frequency is larger for larger rates of changes of the monitored analyte levels at the first frequency.

In certain embodiments, the second frequency is a first value when the rate of change of the monitored analyte levels at the first frequency exceeds a predetermined threshold, wherein the second frequency is a second value when the rate of change of the monitored analyte levels at the first frequency does not exceed the predetermined threshold, wherein the first value is a higher frequency value than the second value.

In certain embodiments, the first frequency is equal to the sampling frequency of the analyte levels derived from the in-vivo positioned analyte sensor.

In certain embodiments, the methods include communicating the stored analyte levels at the second frequency to an analyte monitoring device.

In certain embodiments, the analyte levels monitored at the first frequency is stored for a first period of time, and the stored analyte data logged at the second frequency is logged for a second period of time, wherein the second period of time is longer in duration than the first period of time.

In certain embodiments, the first period of time is less than 1 hour, and the second period of time is greater than 1 hour.

In certain embodiments, the first frequency is less than every 10 minutes, and the second frequency is adjustable to greater than every 10 minutes.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium (also generally referred to herein as computer-readable storage medium or computer-readable medium) and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc. The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The invention claimed is:

1. A glucose monitoring system, the system comprising:
   (1) an on body unit comprising:
      a housing configured to be positioned on a skin of a subject;
      a glucose sensor, at least a portion of which is configured to be positioned under the skin of the subject and in contact with a bodily fluid; and
      sensor electronics coupled with the glucose sensor and disposed within the housing, the sensor electronics comprising a communication module, a processor, and memory for storing a first set of instructions,
      wherein the glucose sensor and the sensor electronics are coupled via conductive contacts prior to positioning the housing on the skin, and
      wherein the first set of instructions, when executed by the processor, cause the processor to:
         generate data indicative of a glucose level based on one or more samples obtained by the glucose sensor at a sampling frequency, and
         wirelessly transmit the data indicative of the glucose level to a reader device;
   (2) an accelerometer configured to generate input information; and
   (3) the reader device comprising:
      processing circuitry coupled with a memory of the reader device, the memory of the reader device storing a second set of instructions that, when executed by the processing circuitry, causes the processing circuitry to:
         process the data indicative of the glucose level, and adjust a variable data setting based at least in part on the input information from the accelerometer while the data indicative of the glucose level continues to be generated and outputted to a display of the reader device, and wherein the variable data setting specifies a logging frequency for storing the one or more samples that were obtained by the glucose sensor at the sampling frequency in the memory at the logging frequency, wherein the logging frequency is different from the sampling frequency.

2. The glucose monitoring system of claim 1, wherein the logging frequency further comprises a duration for which the data indicative of the glucose level is stored in the memory of the reader device.

3. The glucose monitoring system of claim 1, wherein the logging frequency further comprises a rate at which the data indicative of the glucose level is processed on the reader device.

4. The glucose monitoring system of claim 1, wherein the input information from the accelerometer comprises sleep information associated with the subject.

5. The glucose monitoring system of claim 1, wherein the input information from the accelerometer comprises exercise information associated with the subject.

6. The glucose monitoring system of claim 5, wherein the second set of instructions, when executed by the processing circuitry, further causes the processing circuitry to increase the variable data setting during exercise based on the exercise information associated with the subject from the accelerometer.

7. The glucose monitoring system of claim 4, wherein the second set of instructions, when executed by the processing circuitry, further causes the processing circuitry to decrease the variable data setting during sleep based on the sleep information associated with the subject from the accelerometer.

8. The glucose monitoring system of claim 1, wherein the second set of instructions, when executed by the processing circuitry, further causes the processing circuitry to decrease the variable data setting in response to a period of low glucose variability.

9. The glucose monitoring system of claim 1, wherein the second set of instructions, when executed by the processing circuitry, further cause the processing circuitry to adjust the variable data setting in real time.

10. The glucose monitoring system of claim 1, wherein the second set of instructions, when executed by the processing circuitry, further cause the processing circuitry to adjust the variable data setting retrospectively.

11. The glucose monitoring system of claim 1, wherein the second frequency is set to every minute.

12. The glucose monitoring system of claim 1, wherein the housing is a single integral unit configured to rest on the skin of the subject.

13. The glucose monitoring system of claim 1, wherein the communication module of the sensor electronics is configured to wirelessly transmit the data indicative of the glucose level to the reader device according to a Bluetooth communication protocol.

14. The glucose monitoring system of claim 1, wherein the reader device comprises a smartphone.

15. The glucose monitoring system of claim 1, wherein a portion of the glucose sensor is configured to be in fluid contact with interstitial fluid of the subject.

16. The glucose monitoring system of claim 1, wherein the second set of instructions, when executed by the processing circuitry, further causes the processing circuitry to activate an alarm if a glucose level threshold is exceeded.

17. The glucose monitoring system of claim 1, wherein the on body unit further comprises a temperature probe coupled with the sensor electronics.

18. The glucose monitoring system of claim 1, wherein the glucose sensor comprises one or more working electrodes and a counter electrode.

19. The glucose monitoring system of claim 1, wherein the on body unit further comprises a reference voltage generator.

20. The glucose monitoring system of claim 1, wherein the reader device is separate from the accelerometer.

* * * * *